(12) United States Patent
Maor et al.

(10) Patent No.: US 11,651,610 B2
(45) Date of Patent: May 16, 2023

(54) HEART RATE AND RESPIRATION RATE MEASUREMENT USING A FINGERPRINT SENSOR

(71) Applicant: QUALCOMM Incorporated, San Diego, CA (US)

(72) Inventors: Lior Maor, Petah Tikva (IL); Meir Agassy, Ramat Gan (IL); Boaz Castro, Tel Aviv (IL)

(73) Assignee: QUALCOMM Incorporated, San Diego, CA (US)

( * ) Notice: Subject to any disclaimer, the term of this patent is extended or adjusted under 35 U.S.C. 154(b) by 631 days.

(21) Appl. No.: 15/994,808

(22) Filed: May 31, 2018

(65) Prior Publication Data
US 2019/0370518 A1    Dec. 5, 2019

(51) Int. Cl.
*G06V 40/13* (2022.01)
*A61B 8/02* (2006.01)
(Continued)

(52) U.S. Cl.
CPC ............ *G06V 40/1306* (2022.01); *A61B 8/02* (2013.01); *A61B 8/08* (2013.01); *A61B 8/5223* (2013.01); *G06V 40/1382* (2022.01)

(58) Field of Classification Search
CPC ....... A61B 8/02; A61B 8/5223; A61B 5/0816; A61B 8/08; A61B 17/17; A61B 17/1717;
(Continued)

(56) References Cited

U.S. PATENT DOCUMENTS 5,417,215 A * 5/1995 Evans .................. A61B 8/08
                                                    600/442
6,296,610 B1 * 10/2001 Schneider ............ A61B 5/1172
                                                    600/445
(Continued)

OTHER PUBLICATIONS

Schellekens et al., "Time domain acoustic contrast control implementation of sound zones for low-frequency input signals," published on Mar. 25, 2016; 2016 IEEE International Conference on Acoustics, Speech and Signal Processing (ICASSP), 2016, pp. 365-369 (Year: 2016).*

(Continued)

*Primary Examiner* — Chao Sheng
(74) *Attorney, Agent, or Firm* — Qualcomm Incorporated

(57) ABSTRACT

An ultrasonic fingerprint sensor in a mobile device is operated to capture an initial snapshot of reflection from a finger's surface, of acoustic energy transmitted at a first frequency. Additionally, the ultrasonic fingerprint sensor is operated repeatedly to capture over time, a sequence of sets, each set including one or more additional snapshots of reflection from one or more depths within the finger, of acoustic energy transmitted at a second frequency significantly lower than the first frequency. Measurements in the additional snapshots are processed to determine whether any signal oscillating at a rate in a normal range for heart rate or respiration rate is present. When a signal is found, its rate may be used in several ways, e.g. to enable functionality when a fingerprint in the initial snapshot matches a reference fingerprint, or to identify and track a heart rate (or a respiration rate) based on the signal's rate.

21 Claims, 11 Drawing Sheets

(51) Int. Cl.
*A61B 8/08* (2006.01)
*G06V 40/12* (2022.01)

(58) Field of Classification Search
CPC ............ A61B 17/1721; A61B 17/1725; A61B 17/1728; A61B 17/1742; A61B 2034/107; A61B 2034/108; G06K 9/0002; G06K 9/00107; G06V 40/1306; G06V 40/1382
See application file for complete search history.

(56) References Cited

U.S. PATENT DOCUMENTS

| | | | |
|---|---|---|---|
| 8,601,876 B2 | 12/2013 | Schneider et al. | |
| 9,911,184 B2 | 3/2018 | Du et al. | |
| 2014/0219521 A1* | 8/2014 | Schmitt | G06K 9/00107 |
| | | | 382/124 |
| 2014/0352440 A1 | 12/2014 | Fennell et al. | |
| 2014/0355387 A1 | 12/2014 | Kitchens, II et al. | |
| 2015/0023561 A1* | 1/2015 | Hamilton | A61B 8/06 |
| | | | 382/103 |
| 2015/0374240 A1* | 12/2015 | Lee | A61B 5/4866 |
| | | | 600/483 |
| 2017/0231534 A1 | 8/2017 | Agassy et al. | |
| 2018/0360329 A1* | 12/2018 | Chang | A61B 5/0205 |

OTHER PUBLICATIONS

Anthony S., "Qualcomm Unveils its Answer to Touch ID: Ultrasonic Fingerprint Scanning," At Mobile World Congress (MWC) 2015, Mar. 2, 2015, 3 pages.

Press Release: "Qualcomm Announces Advanced Fingerprint Scanning and Authentication Technology," At Mobile World Congress (MWC) 2017, Shanghai, China, Jun. 28, 2017, 6 pages, Retrieved from the Internet: URL: https://www.qualcomm.com/news/releases/2017/06/28/qualcomm-announces-advanced-fingerprint-scanning-and-authentication.

Madhavapeddy S., "Qualcomm Fingerprint Sensors," Jun. 2017, 13 pages, Retrieved from the Internet: URL: https://www.qualcomm.com/media/documents/files/qualcomm-fingerprint-sensors-presentation.pdf.

Triggs R., "Ultrasonic Fingerprint Scanners: How Do They Work?" Jan. 6, 2016, 6 pages.

* cited by examiner

HEART RATE AND RESPIRATION RATE MEASUREMENT USING A FINGERPRINT SENSOR

FIELD

The present disclosure relates to the field of user interfaces. In particular, the present disclosure relates to measuring heart rate and respiration rate with an ultrasonic fingerprint sensor.

BACKGROUND

Fingerprint sensing and matching is a commonly used technique for personal identification or verification. For example, one approach to fingerprint identification involves scanning a sample fingerprint or an image with a biometric reader/sensor and storing the image and/or unique characteristics of the fingerprint image. The characteristics of a sample fingerprint may then be compared to information for reference fingerprints already in a database to determine proper identification of a person, such as for verification purposes.

Ultrasonic fingerprint sensors have become increasingly popular in mobile devices. Such sensors detect ridges and valleys of a user's fingerprint by transmitting ultrasonic signals toward the user's finger and measuring the signals detected thereby. While useful, such ultrasonic sensors may be limited to detecting fingerprints for authenticating users. It is desirable to have apparatuses and methods for using ultrasonic fingerprint sensors, to perform additional functions, as described below.

SUMMARY

The present disclosure relates to methods and apparatuses for measuring heart rate and respiration rate by using ultrasonic fingerprint sensors. In one embodiment, an ultrasonic fingerprint sensor in a mobile device is operated to capture an initial snapshot (also called "ultrasound image") of reflection from a user's finger's surface, of acoustic energy transmitted at a first frequency. Additionally, the ultrasonic fingerprint sensor is operated repeatedly to capture over time, a sequence of sets, each set including one or more additional snapshots of reflection from one or more depths within the user's finger, of acoustic energy transmitted at a second frequency which is significantly lower (e.g. more than 30% lower, or in some embodiments even more than 40% lower) than the first frequency. Measurements in the additional snapshots, which capture movement of subdermal structures within the user's finger, are processed to determine whether any signal oscillating at a rate in a predetermined range for heart rate (or respiration rate) is present. When a signal is found, its rate may be used in several ways, depending on the embodiment, e.g. to enable functionality that is currently disabled in the device (such as the display of the device) when a fingerprint in the initial snapshot matches a reference fingerprint of an authorized user, or to identify and track (and in some embodiments display) the user's heart rate (or respiration rate), based on the signal's rate.

BRIEF DESCRIPTION OF THE DRAWINGS

The aforementioned features and advantages of the disclosure, as well as additional features and advantages thereof, will be more clearly understandable after reading detailed descriptions of embodiments of the disclosure in conjunction with the non-limiting and non-exhaustive aspects of the following drawings. Like numbers are used throughout the figures.

DESCRIPTION OF EMBODIMENTS

Embodiments of methods and apparatuses for measuring heart rate and respiration rate using ultrasonic fingerprint sensors are disclosed. The following descriptions are presented to enable a person skilled in the art to make and use the disclosure. Descriptions of specific embodiments and applications are provided only as examples. Various modifications and combinations of the examples described herein may be readily apparent to those skilled in the art, and the general principles defined herein may be applied to other examples and applications without departing from the scope of the disclosure. Thus, the present disclosure is not intended to be limited to the examples described and shown, but is to be accorded the scope consistent with the principles and features disclosed herein. The word "exemplary" or "example" is used herein to mean "serving as an example, instance, or illustration." Any aspect or embodiment described herein as "exemplary" or as an "example" is not necessarily to be construed as preferred or advantageous over other aspects or embodiments.

When a user places a finger on a platen of a fingerprint sensor, some embodiments of the type described herein operate the fingerprint sensor to generate one or more fingerprints, and also operate the fingerprint sensor while the finger is still on the platen to additionally measure a heart rate and/or a respiration rate. Thus, while the user's finger is still on the platen, the same fingerprint sensor may measure fingerprints during one window of time, measure heart rate in a second window of time, and measure respiratory rate in a third window of time (or alternatively measure the respiratory rate concurrently with the heart rate). The fingerprint may be used for authentication, and the heart rate (or respiration rate) if detected may be used as an indication of liveness of the finger (i.e. determine it is not a spoof). Moreover, the measured heart rate and/or respiration rate may be shown to the user, on a display of a mobile device that contains the fingerprint sensor.

Figure 1A:
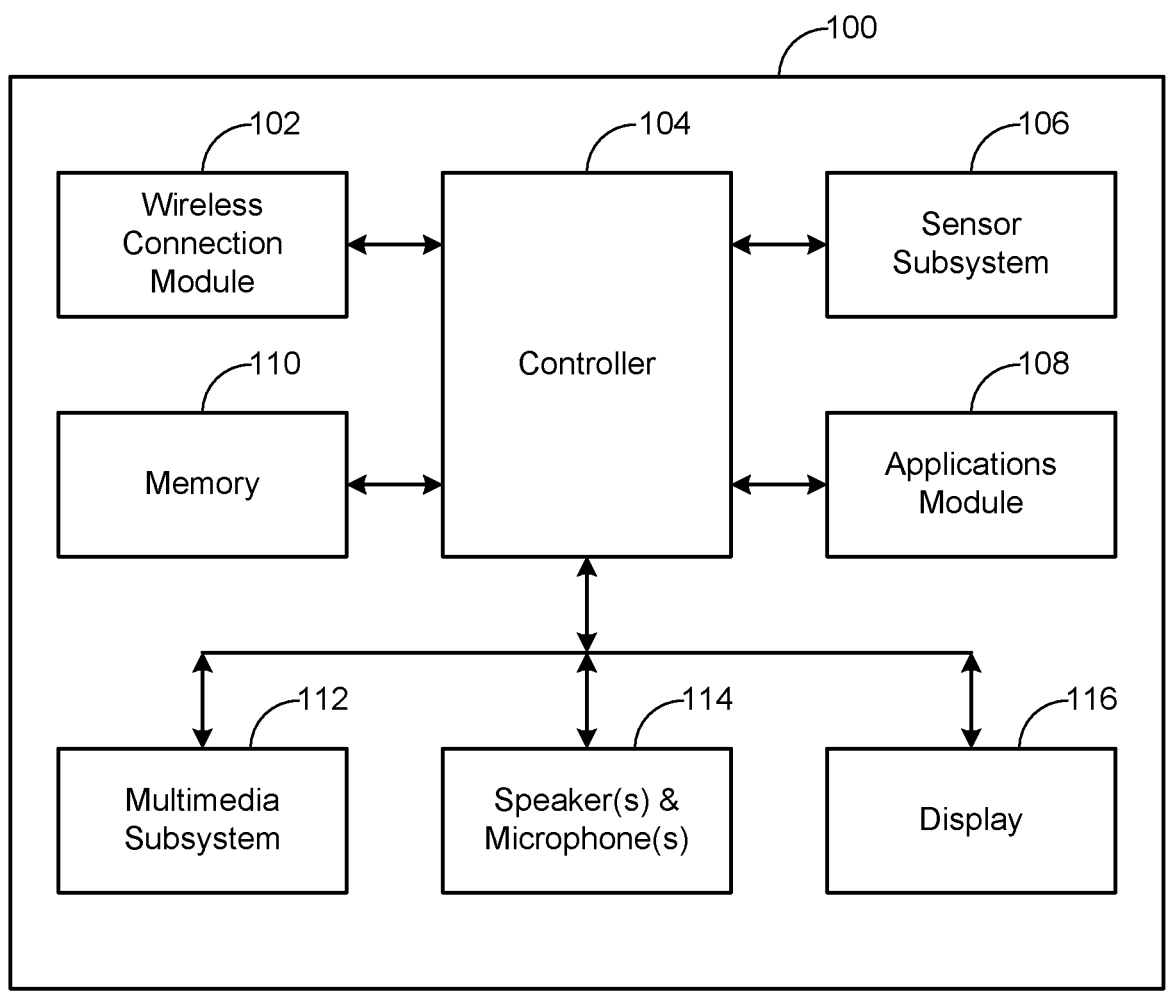
FIG. 1A illustrates an exemplary block diagram of a mobile device according to aspects of the present disclosure.

FIG. 1A illustrates an exemplary block diagram of a mobile device according to aspects of the present disclosure. As shown in FIG. 1A, a mobile device 100 (also referred to as an ultrasonic imaging apparatus) may include wireless connection module 102, controller 104, sensor subsystem 106, memory 110 and applications module 108. In one embodiment, the mobile device 100 of FIG. 1A is implemented as mobile device 700 shown in FIG. 7 and described below. The mobile device 100 of FIG. 1A may optionally include multimedia subsystem 112, speaker(s) and microphone(s) 114, and display 116. In some implementations, the wireless connection module 102 may be configured to support WiFi and/or Bluetooth in a wireless local area network (LAN) or wireless personal area network (PAN). The controller 104 may include one or more processors, software, hardware, and/or firmware to implement various functions described herein. For example, the controller 104 may be configured to implement functions of the mobile device 100 as described herein, e.g. in reference to FIGS. 2A to 9B. The sensor subsystem 106 may be configured to sense and process various sensor input data and produce sensor output data to controller 104. The applications module 108 may include a battery charging circuit and power manager, oscillators, phase lock loops, clock generators and timers.

In some implementations, the sensor subsystem 106 may be configured to sense and detect a swipe motion in low power conditions. For example, the sensor subsystem 106 may be configured to include a sensor having a plurality of sensor pixels, such as an 80 pixels by 180 pixels detector configuration, to determine a swipe motion of a finger or a stylus. In some other implementations, different sensor configurations with different sensor areas may be employed.

In certain embodiments, mobile device 100 may include a wireless transceiver that is capable of transmitting and receiving wireless signals via a wireless antenna over a wireless communication network. Some embodiments may include multiple wireless transceivers and wireless antennas to enable transmitting and/or receiving signals according to corresponding multiple wireless communication standards such as, for example, versions of IEEE Std. 802.11, CDMA, WCDMA, LTE, UMTS, GSM, AMPS, Zigbee and Bluetooth, etc.

In various embodiments, controller 104 may be configured to execute computer-readable instructions stored in memory 110 such as on a computer-readable storage medium, such as RAM, ROM, FLASH, or disc drive, just to name a few examples. More specifically, the instructions may be executable by one or more processors, specialized processors, or DSPs of controller 104. Memory 110 may include a non-transitory computer-readable memory and/or a computer-readable memory that stores software code (programming code, instructions, etc.) that are executable by the processors and/or DSPs to perform functions described herein. In some embodiments, memory 110 supports (and is used to implement), means for storing data, including sets of snapshots of reflected acoustic energy and the measurements from the snapshots. Controller 104 may execute instructions in memory 110 to perform one or more aspects of processes/methods discussed below in connection with FIGS. 2A, 3, 4, 5 and 6.

In some implementations, a user interface may include any one of several devices such as, for example, multimedia subsystem 112, speakers and microphones 114, display 116, etc. In a particular implementation, the user interface may enable a user to interact with one or more applications hosted on mobile device 100. For example, devices may store digital signals in memory 110 to be further processed by controller 104 in response to an action from a user. Similarly, applications hosted on mobile device 100 may store digital signals in memory 110 to present an output signal to a user.

Mobile device 100 may also include a camera for capturing still or moving imagery. The camera may include, for example, an imaging sensor (e.g., charge coupled device or CMOS imager), lens, analog to digital circuitry, frame buffers, etc. In some implementations, additional processing, conditioning, encoding or compression of signals representing captured images may be performed by controller 104. Alternatively, a video processor may perform conditioning, encoding, compression or manipulation of signals representing captured images. Additionally, the video processor may decode/decompress stored image data for presentation on display 116 of mobile device 100.

Figure 1B:
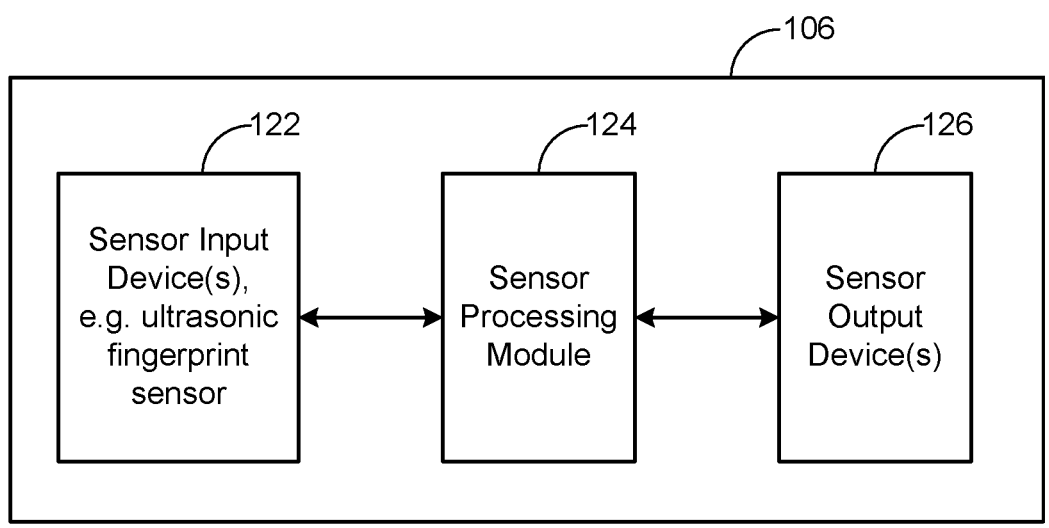
FIG. 1B illustrates an exemplary implementation of the sensor subsystem of the mobile device of FIG. 1A according to aspects of the present disclosure.

FIG. 1B illustrates an exemplary implementation of the sensor subsystem of the mobile device 100 of FIG. 1A according to aspects of the present disclosure. Sensor subsystem 106 may generate analog signals that may be converted to digital signals using an analog-to-digital converter (ADC). Alternatively, sensor subsystem 106 may generate digital signals. The digital signals are stored in memory 110 and processed by controller 104 in support of one or more applications such as, for example, applications related to activating a device based on detection of a fingerprint image.

As shown in FIG. 1B, the sensor subsystem 106 may include one or more sensor input devices 122, sensor processing module 124, and one or more sensor output devices 126. The one or more sensor input devices 122 may include an ultrasonic fingerprint sensor for capturing fingerprints and/or measuring heart rate and respiration rate as described herein, e.g. in association with FIG. 1A. The one or more sensor input devices 122 may also include one or more other ultrasonic sensors, temperature and moisture sensors, capacitive sensors, microphones, ultrasound microphone arrays, photo detectors, image sensors, touch sensors, pressure sensors, chemical sensors, gyroscopes, accelerometers, magnetometers, GPS and compass. The sensor processing module 124 may be configured to perform one or more of the following functions, including but not limited to: input sensor selection and control, synchronization and timing control, signal processing, sensor platform performance estimation, sensor optimization, sensor fusion, and output sensor/device selection and control. The one or more sensor output devices 126 may produce one or more ultrasonic, voice, visual, biometric, nearness, presence, pressure, stability, vibration, location, orientation, heading, kinetics, electrical and chemical signals. The sensor subsystem 106 may be configured to implement functions of enabling operation of a mobile device, e.g. based on processing one or more two-dimensional ultrasound images of a finger's surface and subdermal structures within the finger, as described in reference to FIGS. 2A, 3, 4, 5 and 6. In some implementations, one or more capacitive sensors may be configured to measure capacitance values of a touch of the finger.

The sensor processing module 124 may be configured to process sensor input data from the one or more sensor input devices 122, and produce output commands or signals to the one or more sensor output devices 126. According to aspects of the present disclosure, direct user inputs may be used to predictably manipulate power control behavior. In some embodiments, a mobile device may be configured to accept user commands (via direct, voice/aural and/or visual inputs) and be configured to sense a multitude of use, use environment and use contexts. In some implementations, an ultrasonic fingerprint sensor can be used to recognize a user's gestures, e.g. movements of a finger such as left/right/up/down, single or double taps, or press-and-hold motions that can be used to activate certain functions more quickly such as taking pictures.

In some implementations, the sensor processing module 124 may include an application-specific integrated circuit (ASIC) that includes circuitry such as a plurality of voltage regulators for generating a plurality of power supply voltages; memory, finite-state machines, level shifters and other associated circuitry for generating control signals to an ultrasonic fingerprint sensor (see FIG. 9B) which includes an ultrasonic transmitter and an ultrasonic receiver (which in turn includes an ultrasonic sensor pixel circuit array); circuitry for generating transmitter excitation signals input to the ultrasonic transmitter to identify a frequency of acoustic energy to be transmitted, range-gate delay signals input to the ultrasonic receiver to determine depth at which reflection of the acoustic energy is to be measured, diode bias signals and receiver bias signals to the ultrasonic fingerprint sensor; circuitry for analog signal conditioning, analog-to-digital conversion and digital processing of the received pixel output signals from the ultrasonic receiver; and interface circuitry for sending digital output signals to an applications processor of a mobile device. The applications processor may execute the methods described in this disclosure.

In other implementations, in addition to the ASIC circuitry described in the prior paragraph, the ASIC may also include a microcontroller to autonomously execute one or more initial stages of methods and processes described below in reference to FIGS. 2A, 3, 4, 5 and 6 locally on the ASIC. For low power operations, it may be desirable that the microcontroller make determinations before requesting and enlisting the processing resources of an applications processor and/or data processor and/or other components in mobile device 100.

In yet other implementations, in addition to the microcontroller and ASIC circuitry noted above, the ASIC may also include an ultrasonic fingerprint sensor's associated circuitry such as row-drivers and column-gate drivers to scan pixel circuits in the ultrasonic sensor pixel circuit array (in the ultrasonic receiver). In these implementations, the ASIC may execute the functions of sensing the output signals of pixel circuits at (x,y) locations in a two-dimensional array, in addition to the functions of finger presence detection and other functions described herein.

Figure 2A:
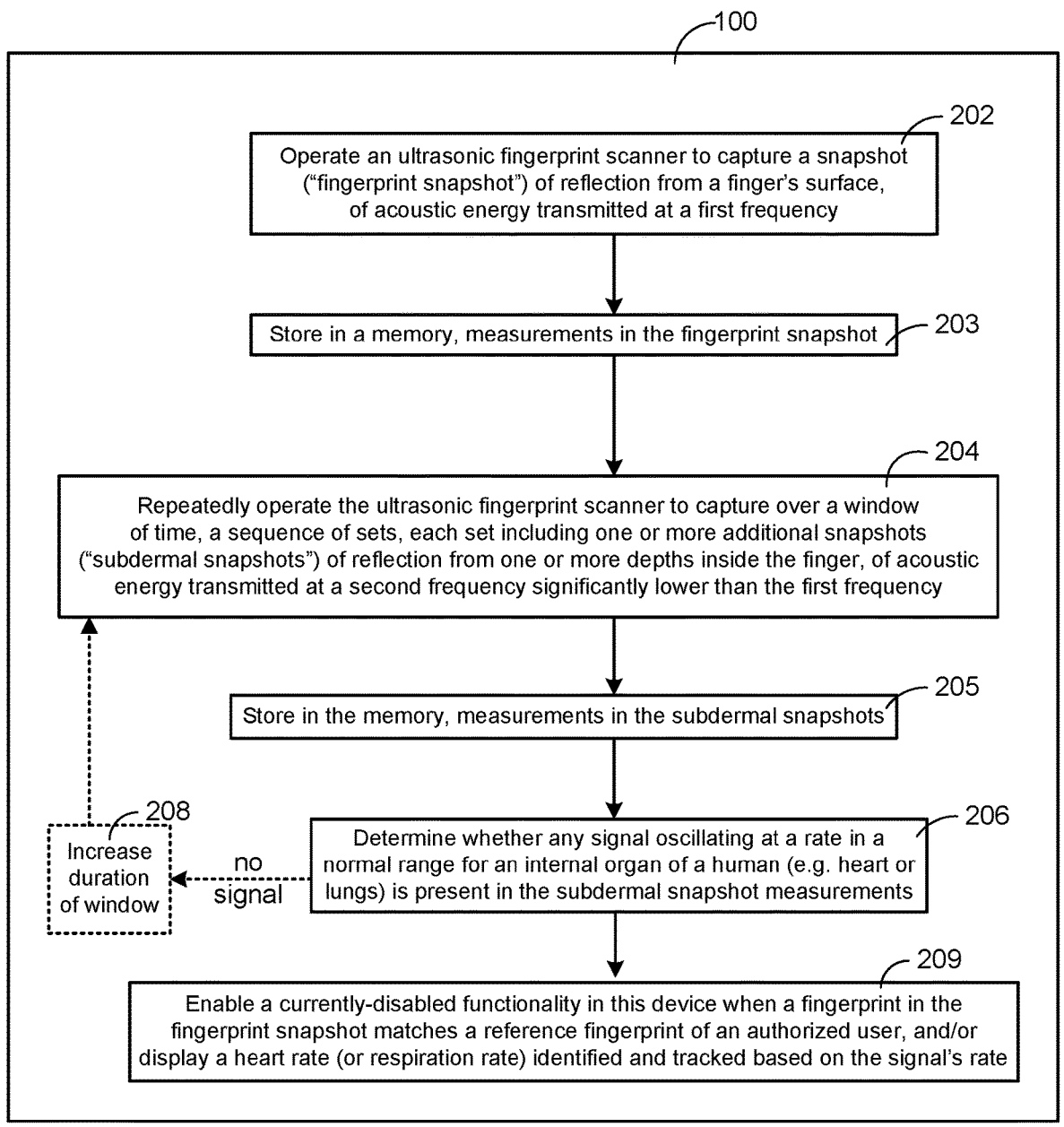
FIG. 2A illustrates an exemplary implementation of measuring a heart rate or a respiration rate according to aspects of the present disclosure.
Figure 2B:
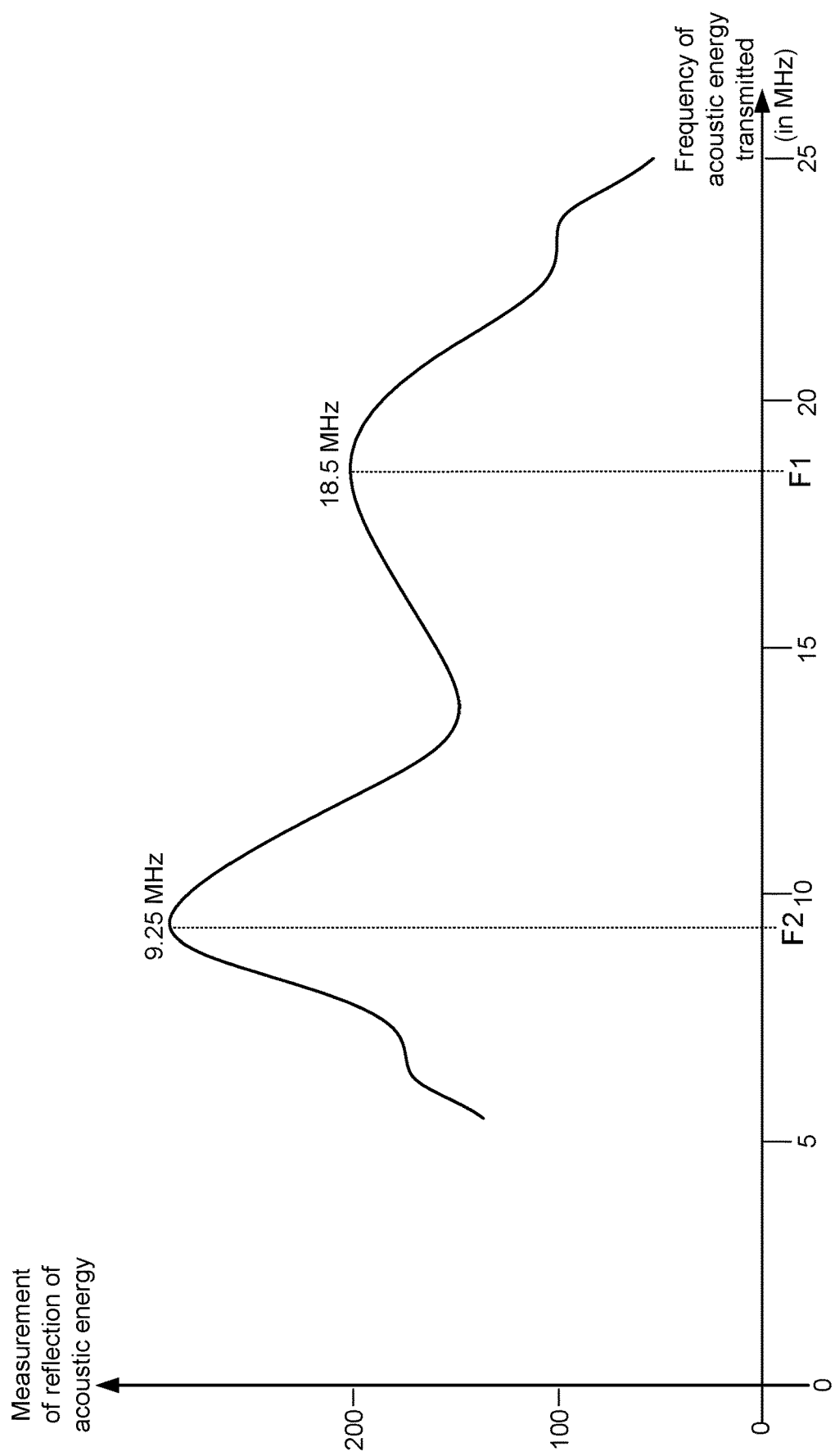
FIG. 2B illustrates a graph used to obtain two frequencies F1 and F2 specified to an ultrasonic fingerprint sensor for generation of fingerprint snapshots and subdermal snapshots respectively according to aspects of the present disclosure.
Figure 2C:
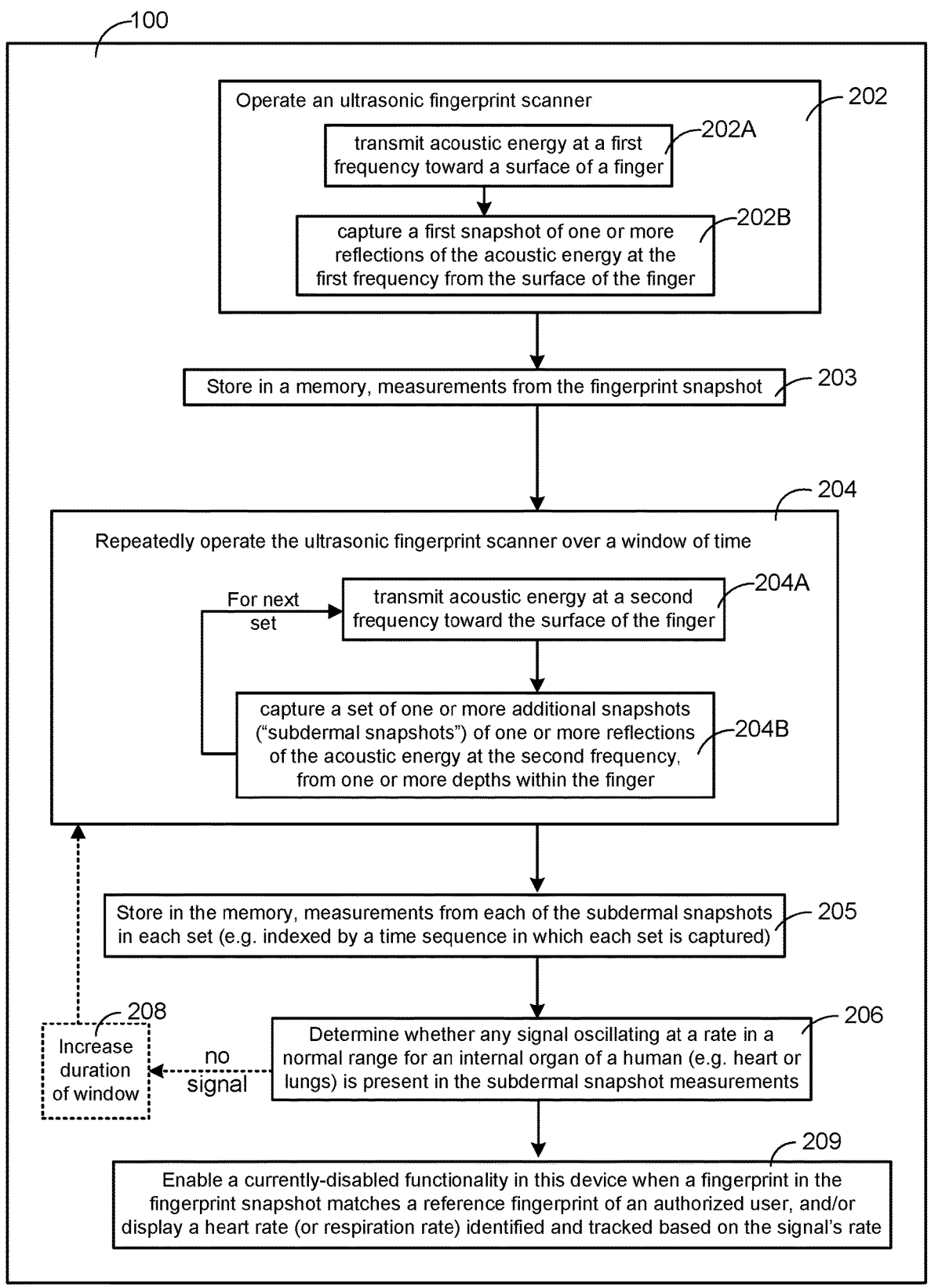
FIG. 2C illustrates blocks 202A and 202B that implement block 202 of FIG. 2A and blocks 204A and 204B that implement block 204 of FIG. 2A in an exemplary implementation according to aspects of the present disclosure.

FIG. 2A illustrates an exemplary implementation of measuring heart rate and respiration rate using an ultrasonic fingerprint sensor, according to aspects of the present disclosure. In this exemplary implementation, a sequence of sets of one or more snapshots (or ultrasound images) at one or more depths within a user's finger may be captured sequentially in time by the ultrasonic fingerprint sensor, and a controller may be configured to use changes over time in the sequence of sets, due to movements of one or more subdermal structures in the user's finger, to determine the user's heart rate and/or respiration rate.

In one embodiment, controller 104 (see FIG. 1A) responds to placement of a user's finger adjacent to an ultrasonic fingerprint sensor in sensor input device(s) 122 (see FIG. 1B), by operating the ultrasonic fingerprint sensor. Specifically, the ultrasonic fingerprint sensor is operated to transmit acoustic energy at a first frequency toward a surface of the finger (e.g. see block 202A in FIG. 2C) and capture one or more initial snapshots (also called "fingerprint snapshots") of one or more reflections of the acoustic energy from the finger's surface (e.g. see block 202B in FIG. 2C). Depending on the embodiment, the ultrasonic fingerprint sensor may be operated indirectly by controller 104 sending commands to sensor processing module 124 of FIG. 1B. In some embodiments, the acoustic energy is transmitted by the ultrasonic fingerprint sensor as an unmodulated pulse having a predetermined number of cycles of a sine wave at the first frequency. The just-described operation, which may be performed by controller 104 in some embodiments of mobile device 100 is illustrated by block 202 in FIG. 2A (which may be implemented as blocks 202A and 202B in FIG. 2C).

The first frequency specified by controller 104 in block 202 may be determined ahead of time in some embodiments to be high enough for acoustic energy sensed in the ultrasonic fingerprint sensor's pixel circuits, at (x,y) locations in a two-dimensional array (e.g. 80×180 in size), as measurements that have sufficient spatial resolution to identify lines representing ridges and valleys on the finger's surface. One embodiment of controller 104 specifies in block 202, as the ultrasonic transmitter's frequency, a frequency F1 (e.g. 18.5 MHz illustrated in FIG. 2B) which is experimentally determined, based on occurrence of a local maxima in a graph of signal strength (measured in reflection of acoustic energy) on the y-axis and frequency of the acoustic energy transmitted on the x-axis (see FIG. 2B). In some implementations, controller 104 may be configured to obtain the ultrasonic transmitter's frequency specified in block 202, based on variation of a current temperature from a reference temperature at which an initial value for frequency F1 is experimentally determined (e.g. 18.5 MHz illustrated in FIG. 2B).

Moreover, to capture the initial snapshots in block 202, controller 104 may specify a time delay (also referred to as range gate delay) between operating the ultrasonic receiver and the ultrasonic transmitter, based on an amount of time needed for sound to travel a first distance from the ultrasonic transmitter to the finger's surface (which may be placed on a surface of a platen), and a second distance from the finger's surface to the ultrasonic receiver.

On completion of block 202, measurements by the ultrasonic fingerprint sensor which are included in one or more initial snapshots, may be stored in a memory of mobile device 100, e.g. in memory 110 in FIG. 1A. The just-described storage operation, which may be performed by controller 104 in some embodiments of mobile device 100 is illustrated by block 203 in FIG. 2A. Also, controller 104 may be configured to process the one or more initial snapshot(s) in memory 110 in a normal manner, e.g. to extract a fingerprint therefrom, and compare the extracted fingerprint to a reference fingerprint of an authorized user. If the extracted fingerprint matches the reference fingerprint, controller 104 may authenticate the user and enable the user to gain access to mobile device 100. In addition to authenticating a user based on an extracted fingerprint, certain embodiments of controller 104 may be configured to determine liveness of the user's finger (e.g. find a signal oscillating at a heart rate or at a respiration rate) as described herein, before enabling access to mobile device 100.

Additionally, controller 104 may be configured to further operate the ultrasonic fingerprint sensor repeatedly (as illustrated by block 204 in FIG. 2A), to capture over a window of time (e.g. of 3 seconds duration), a sequence of sets, each set including one or more additional snapshots ("subdermal snapshots") of reflection from one or more depths within the user's finger, of acoustic energy transmitted (e.g. also as an unmodulated pulse having a predetermined number of cycles of a sine wave) at a second frequency by the ultrasonic fingerprint sensor. The just-described operation, which may be performed by controller 104 in some embodiments of mobile device 100 is illustrated by block 204 in FIG. 2A (which may be implemented as blocks 204A and 204B in FIG. 2C).

In block 204 in FIG. 2A (and more particularly in block 204A in FIG. 2C), controller 104 is configured to not specify the first frequency (which is specified in block 202), because any reflections of acoustic energy at the first frequency from the one or more subdermal structures in the finger have intensities at the ultrasound receiver that are too low to be distinguishable from noise. Specifically, there is a tradeoff between resolution and scan depth: to obtain better resolution, the frequency needs to be increased, however, as the frequency increases the SNR decreases (the signal is attenuated) and the acoustic energy cannot travel deeper into the finger. Hence, controller 104 is configured in some embodiments, to specify in block 204, a second frequency that is sufficiently low for the reflections of acoustic energy from the one or more subdermal structures to have intensities at the ultrasound receiver sufficiently high to be distinguishable from noise.

The second frequency specified by controller 104 in block 204 in FIG. 2A (and more particularly in block 204A in FIG. 2C), may be determined ahead of time in some embodiments to be significantly lower (e.g. more than 30% lower, or in some embodiments even more than 40% lower) than the first frequency used in block 202. In several embodiments, the second frequency is predetermined to be low enough for acoustic energy to pass through skin and reach subdermal structures within the finger. One embodiment of controller 104 specifies in block 204, as the ultrasonic transmitter's frequency, a frequency F2 (e.g. 9.25 MHz illustrated in FIG. 2B) which is also experimentally determined, based on occurrence of another local maxima in the graph of signal strength (measured in reflection of acoustic energy) on the y-axis and frequency of the acoustic energy transmitted on the x-axis (see FIG. 2B). In the specific embodiment illustrated in FIG. 2B, frequency F2 (which is used to determine oscillation of an internal organ) is precisely half of the frequency F1 (which is used to create a fingerprint), although this relationship between these two frequencies is approximate in other embodiments. In a manner similar or identical to block 202, some implementations of controller 104 may be additionally configured to obtain the ultrasonic transmitter's frequency specified in block 204, based on variation of the current temperature from a reference temperature at which the initial value for frequency F2 is experimentally determined (e.g. 9.25 MHz illustrated in FIG. 2B).

Moreover, to capture the additional snapshots in block 204, controller 104 may specify one or more time delays (or range gate delays), based on an amount of time needed for sound to travel a first distance from the ultrasonic transmitter to one or more depths in the finger, and a second distance from the one or more depths in the finger to the ultrasonic receiver. The one or more depths in the finger may be selected to be, for example, in a range centered at half the thickness of a human finger (e.g. 4 mm), with the range having a width also of half the thickness of the human finger (e.g. 4 mm also). The number of depths used in block 204 may be configured ahead of time, e.g. based on computational power and memory of mobile device 100.

In some embodiments, controller 104 is implemented with a system clock of 128 MHz, and converts each depth to a time delay (or range gate delay, abbreviated as RGD) based on speed of sound at 1500 meters per second as follows:

Depth [mm]=RGD/2/128 [MHz]*1500 [m/s]*1e3

RGDs=[500,1100]

Depth [mm]=[500,1100]/2/128$e6$*1500*1e3=[2.9, 6.4]

The values 500 and 1100 of RGD shown above are number of cycles, of a clock oscillating at 128 MHz. However, it should be recognized that any suitable clock speed may be used to determine the RGD. In an illustrative embodiment, controller 104 uses an RGD of 650-800 corresponding to a depth of ~4-4.5 mm. The just-described values of 650 and 800 are also expressed in number of clock cycles at 128 MHz. Some embodiments may use RGD of 4.5-8 μsec.

On completion of one or more loops of operation of block 204, measurements by the ultrasonic fingerprint sensor which are included in one or more additional snapshots, may be stored in a memory of mobile device 100, e.g. in memory 110 in FIG. 1A. The just-described storage operation, which may be performed by controller 104 in some embodiments of mobile device 100 is illustrated by block 205 in FIG. 2A.

Controller 104 may be configured to process the one or more additional snapshot(s) in memory 110 in block 206 (FIG. 2A), to determine whether any signal oscillating at a rate in a predetermined range for an internal organ of a human is present. In one illustrative example, the internal organ is a heart, and the predetermined range is selected to have a lower limit of 40 beats per minute (or 40 cycles per minute) and an upper limit of 200 beats per minute (or 200 cycles per minute). In another illustrative example, the internal organ is human lungs, and the predetermined range is selected to have a lower limit of 8 breaths per minute (or 8 cycles per minute) and an upper limit of 40 breaths per minute (or 40 cycles per minute). Other examples of predetermined ranges for a human organ as described herein may use lower limits and upper limits that approximate the just-described values, for example to within 10%. Depending on the embodiment, controller 104 may be configured to respond to finding a signal in block 206, by using the signal's oscillation rate in several ways as per block 209 in FIG. 2A. For example, block 209 may enable functionality that is currently disabled in mobile device 100 (such as turning on power to display 116 in FIG. 1A), when a fingerprint in an initial snapshot (see block 202) is found to match a reference fingerprint of an authorized user, or to identify and track (and in some embodiments, show on display 116) as a current value of the user's heart rate (or respiration rate), the signal's oscillation rate.

In some implementations, when controller 104 finds no signal in block 206, controller 104 is configured to operate block 208 in which duration of the above-described window (see block 204) is increased, e.g. by 1 second. When block 206 is again operated, on measurements captured over the increased duration window, controller 104 may find a signal. The just-described loop, between blocks 208, 204, 205 and 206 may be repeated a predetermined number of times, e.g. 9 times (to reach a final window size of 12 seconds). If controller 104 does not detect a signal (or a predetermined number of signals) during the loop, controller 104 may determine that the object placed proximate to the fingerprint sensor is not a live finger or extremity (i.e., the object is a spoof). However, if controller 104 detects a signal (or a predetermined number of signals) in one or more of the loops, controller 104 may determine that the object placed proximate to the fingerprint sensor is a live finger of the user. In some embodiments, controller 104 which operates one or more of blocks 202-209 in FIG. 2A supports (and is used to implement), means for controlling the operations of the mobile device and the ultrasonic fingerprint sensor, as well as means for controlling the operations of the methods described herein.

Figure 3:
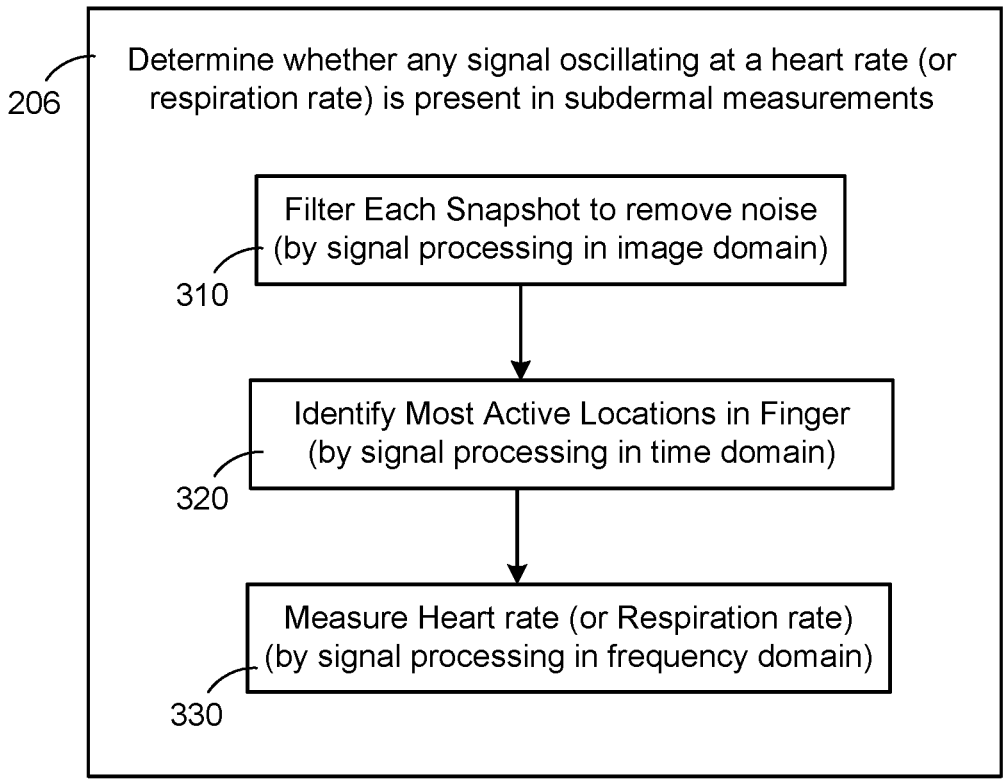
FIG. 3 illustrates blocks 310, 320 and 330 that together implement block 206 of FIG. 2A according to certain aspects of the present disclosure.
Figure 4:
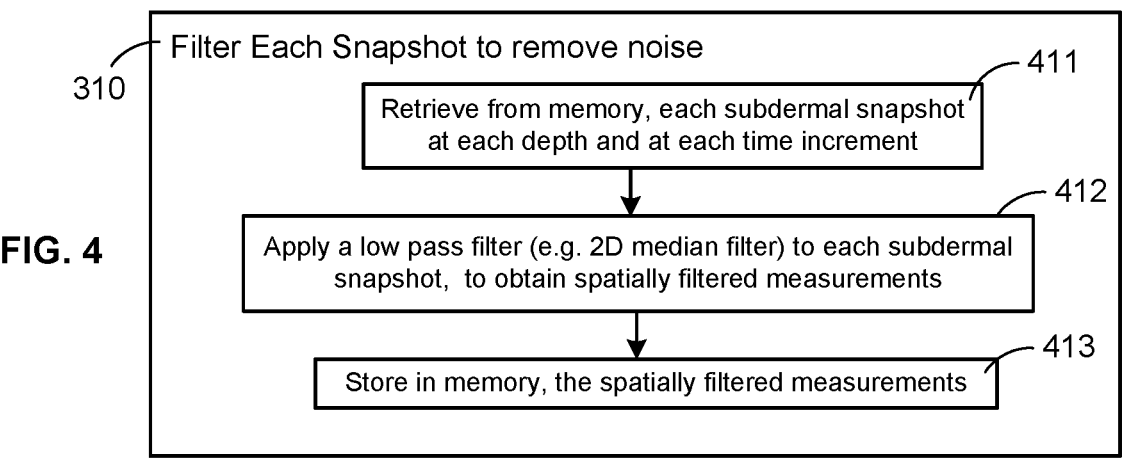
FIG. 4 illustrates an example of filtering each snapshot to remove noise according to aspects of the present disclosure.
Figure 5:
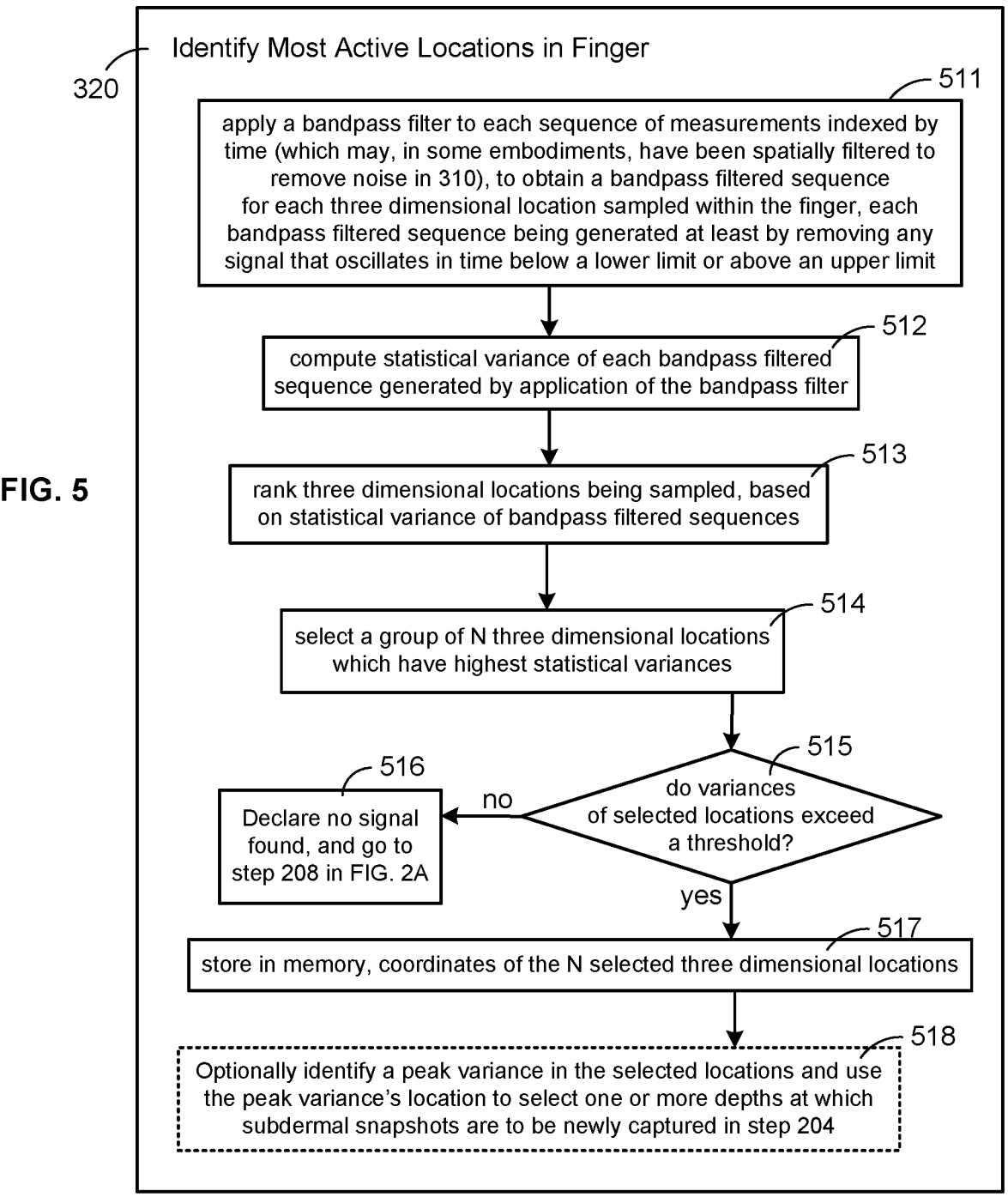
FIG. 5 illustrates an example of identifying most active locations according to aspects of the present disclosure.
Figure 6:
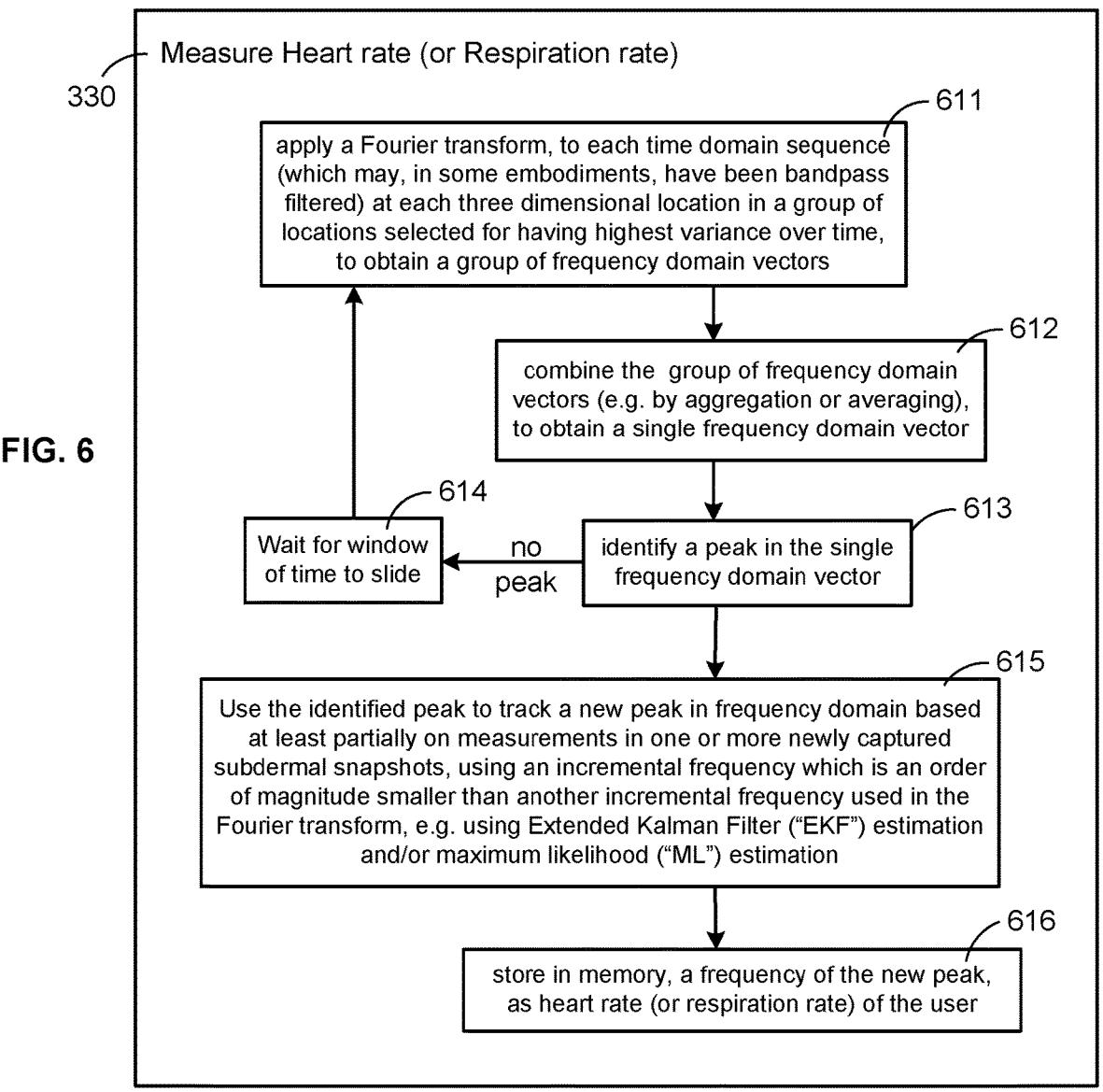
FIG. 6 illustrates measuring a heart rate or a respiration rate according to aspects of the present disclosure.

In some embodiments of controller 104, block 206 which determines whether any signal oscillating at a heart rate (or respiration rate) is present in the additional measurements (captured in block 204) may be operated, by operating one or more of blocks 310-330 illustrated in FIG. 3. Specifically, in block 310, controller 104 may be configured to filter each snapshot to remove noise (e.g. by signal processing in image domain). Thereafter, in block 320, controller 104 may be configured to identify most active locations (wherein blood flow is likely) in the finger (e.g. by signal processing in time domain). Finally, in block 330, controller 104 may be configured to measure heart rate or respiration rate (e.g. by signal processing in frequency domain).

Controller 104 may be configured to operate block 310 (FIG. 3) by operating one or more of blocks 411-413 (FIG. 4) as follows. In block 411, controller 104 may be configured to retrieve from memory 110, all snapshots within a time window (e.g. of 3 second in duration) that have been stored by block 205 (FIG. 2A). In block 412, controller 104 may be configured apply a low pass filter, such as a 2D median filter, to each snapshot, to obtain spatially filtered measurements. In block 413, controller 104 may be configured to store in memory 110, the spatially filtered measurements obtained by block 412.

As noted above in reference to block 204 (see FIGS. 2A and 2C), the ultrasonic fingerprint sensor is operated repeatedly over a window of time, to capture a sequence of sets, and each set includes one or more snapshots at each of one or more depths (e.g. measured along z axis). Hence, measurements in the sequence may be indexed by time across the snapshots, e.g. at a specific location in the finger whose x,y coordinates are determined by a specific pixel circuit that measures acoustic energy at an (x,y) location in a two-dimensional array in the ultrasound receiver, and whose z coordinate is determined by depth in the finger (in turn determined by a time delay, also referred to as range gate delay). Thus, for each (x, y, z) location which is sampled in the finger (also called "subdermal location"), memory 110 contains a sequence of measurements indexed by time, which is stored by block 205 (e.g. see FIG. 2C). Additionally, at each (x, y, z) location sampled in the finger, there may be a sequence of spatially filtered measurements indexed by time, which is stored in memory 110 by block 413 (if operated, depending on the embodiment).

In some embodiments, controller 104 may be configured to operate block 320 (FIG. 3) by operating one or more of blocks 511-517 and optional block 518 (FIG. 5) as follows.

In block 511, controller 104 may be configured to apply a bandpass filter to each sequence of measurements indexed by time (which may, in some embodiments, have been spatially filtered to remove noise in block 310). The result of operation of block 511 is a bandpass filtered sequence for each location sampled within the finger, and each bandpass filtered sequence is generated at least by removing (or reducing the amplitude of) any signal that oscillates in time below a lower limit or above an upper limit.

In one illustrative embodiment, controller 104 operates block 511 to determine whether any signal oscillating at a human heart rate is present, and uses 40 beats per minute as the lower limit of the bandpass filter and 200 beats per minute as the upper limit. In another illustrative embodiment, controller 104 operates block 511 to determine whether any signal oscillating at a human respiration rate is present, and uses 8 breaths per minute as the lower limit of the bandpass filter and 40 breaths per minute as the upper limit.

In still another embodiment, block 206 (see FIG. 2A) is implemented to contain therein two parallel branches that are respectively used to determine heart rate and respiration rate simultaneously. These two parallel branches start in a common block 310, followed by two copies of block 320 to identify two different sets of most active locations in the finger (see FIG. 3) for use in determining heart rate and respiration rate respectively (e.g. by applying two bandpass filters, with corresponding predetermined ranges of 40-200 cycles per minute and 8-40 cycles per minute). The two copies of block 320 are followed by corresponding two copies of block 330 used to find respective peaks in the frequency domain, thereby to identify the heart rate and respiration rate. In one such embodiment, a time window is 8 seconds in duration, and both heart rate and respiration rate are determined simultaneously, from a common set of measurements. In such an embodiment, heart rate is determined as soon as measurements are accumulated for 3 seconds, although determination of respiration rate takes an additional 5 seconds (so that sufficient measurements are accumulated in its time window of 8 seconds). In other embodiments, a different time window may be used (e.g., 16 seconds) to provide sufficient time to measure the respiratory rate.

Yet another embodiment may be configured to operate block 206 (and therefore block 320) twice, a first time to determine heart rate and a second time to determine respiration rate, and these rates may be determined based on measurements in respective time windows that do not overlap one another.

In many such embodiments, wherein signals of both heart rate and respiration rate are determined from subdermal snapshots in a finger, most of the blocks and operations described herein may be operated and/or performed similarly or identically to one another, except for the above-noted difference in upper and lower limits of the predetermined ranges.

In block 512, controller 104 may be configured to compute variance of each bandpass filtered sequence generated in block 511, by application of the bandpass filter. For example, in one illustrative embodiment, controller 104 computes variance as follows:

$$\frac{1}{T}\sum_{t=0}^{T-1}(x[t]-\mu_x)^2$$

where T is number of samples (or measurements) in a sequence along the time axis, t. Thereafter, in block 513, controller 104 ranks the subdermal locations being sampled (or probed), based on variance of corresponding bandpass filtered sequences, which is computed in block 512. Next, based on the rank ordering in block 513, controller 104 selects in block 514, a predetermined number N of subdermal locations (e.g. 1000 subdermal locations), which have the highest statistical variances (and hence most active).

Thereafter, in block 515, controller 104 may be configured to perform a test (e.g. check if variances of the N selected locations exceed a threshold or other such test) related to noise. If the test in block 515 is not met, block 516 may be operated to declare that no signal is found, followed by going to block 208 (see FIG. 2A, described above). When the test in block 515 is met, block 517 may be operated, to store in memory 110, coordinates of the N selected locations. Finally, in an optional block 518, the N selected locations may be used to identify location of peak variance, and the peak variance's location may be used to select a central depth and one or more depths around the central depth, for use in operating the ultrasound receiver to capture subdermal snapshots in a next operation of block 204 (see FIG. 2A, described above). In such embodiments, an initial set of depths may be predetermined to be in the range [−150,150] around a center RGD of ~650, in blocks of 50 or less.

Controller 104 may be configured to operate block 330 (FIG. 3) by operating one or more of blocks 611-616 (FIG. 6) as follows. In block 611, controller 104 may be configured to apply a Fourier transform, to each time domain sequence (which may, in some embodiments, have been bandpass filtered in block 511 as described above) at each subdermal location in the N subdermal locations selected for having highest variance over time (e.g. as described above in block 514 (FIG. 5). On completion of block 611, controller 104 may obtain N frequency domain vectors. Thereafter, in block 612, controller 104 may be configured to combine the N frequency domain vectors, e.g. by aggregation (or by averaging), to obtain a single frequency domain vector. Subsequently, in block 613, controller 104 may be configured to identify a peak in the single frequency domain vector. The peak is tested in block 613 to have sufficient signal-to-noise ratio, and if not then controller 104 may go to block 614 to wait for a new set of subdermal snapshots to become available (e.g. by sliding the time window forward, when an iteration of sampling is completed).

In some embodiments, block 613 may be configured to calculate an estimated signal-to-noise ratio and a quality factor, to determine the presence of a peak (and hence a signal oscillating at a rate in the predetermined range for an internal organ of a human, as per block 206) based on the following formulae.

$$\text{Peak} \triangleq Y(f = f_c)$$

$$\text{Noise} \triangleq Y(f \neq f_c)$$

$$SNR_{est} = \frac{Peak^2}{MeanNoise^2} \cdot \frac{\pi}{2N_{fft}}$$

$$QF_{est} = \frac{Peak - Mean(Noise)}{Std(Noise)}$$

When a peak is found, in some embodiments, controller 104 may be configured to operate block 615, wherein the identified peak is used to track a new peak in the frequency domain. The tracking in block 615 is performed in the frequency domain on measurements in one or more newly captured subdermal snapshots, using an incremental frequency which is an order of magnitude smaller than another incremental frequency used in the Fourier transform, e.g. using Extended Kalman Filter ("EKF") estimation and/or maximum likelihood ("ML") estimation. A frequency of the new peak obtained by tracking in block 615 is stored in block 616 by controller 104 in memory 110, for use as a heart rate of the user (or a respiration rate of the user), e.g. in block 209 (FIG. 2A).

The frequency stored in memory 110 by block 616 may be shown by some embodiments, on display 116 of mobile device 100 (FIG. 1A), e.g. as a heart rate or a respiration rate. Depending on the embodiment, the frequency stored in memory 110 by block 616 may be used by controller 104 to determine liveness and based thereon enable power to display 116, as described above. In some embodiments, a time window of at least 3 seconds in duration is used to determine heart rate as described above. Hence, after a finger is placed on platen 40 of an ultrasonic fingerprint sensor 10 (FIGS. 8A-8C) in such embodiments, a pulse of low ultrasound frequency is repeatedly transmitted towards the finger for at least 3 seconds before the display is powered up and heart rate displayed thereon (if the user's fingerprint is determined to be authentic).

Figure 7:
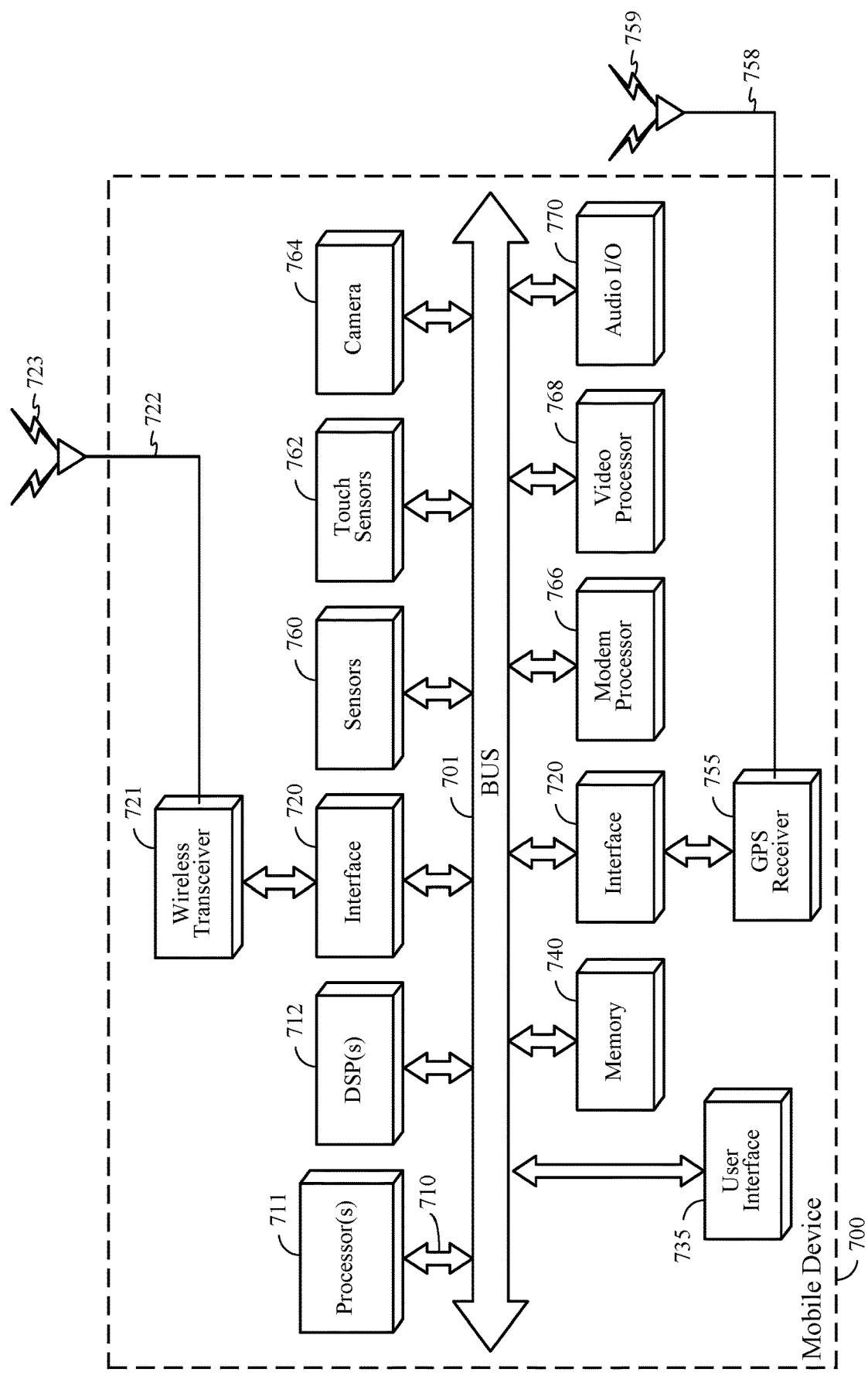
FIG. 7 illustrates an exemplary block diagram of a device that may be configured to implement measuring heart rate and respiration rate using an ultrasonic fingerprint sensor according to aspects of the present disclosure.

In some embodiments, block 615 may be configured to calculate estimates using a quadratic interpolation method, based on a peak and its two nearest samples as follows.

$$y1=Xa(k-1);$$

$$y2=Xa(k);$$

$$y3=Xa(k+1);$$

$$d=(y3-y1)/(2*(2*y2-y1-y3));$$

$$f\_interp=f(k)+d*df;$$

where:
k is the peak index
Xa(k) is the peak value
f(k) is the frequency of the peak
df is the frequency spacing
f_interp is the final interpolated frequency FIG. 7 illustrates an exemplary block diagram of a device that may be configured to implement the methods and apparatuses for measuring fingerprints, heart rate, and/or respiration rate using an ultrasonic fingerprint sensor, according to aspects of the present disclosure. A device that implements measuring (and in some embodiments showing) heart rate and/or respiration rate using an ultrasonic fingerprint sensor may include one or more features of mobile device 700 shown in FIG. 7. In certain embodiments, mobile device 700 may include a wireless transceiver 721 that is capable of transmitting and receiving wireless signals 723 via wireless antenna 722 over a wireless communication network. Wireless transceiver 721 may be connected to bus 701 by a wireless transceiver bus interface 720. Wireless transceiver bus interface 720 may, in some embodiments be at least partially integrated with wireless transceiver 721. Some embodiments may include multiple wireless transceivers 721 and wireless antennas 722 to enable transmitting and/or receiving signals according to a corresponding multiple wireless communication standards such as, for example, versions of IEEE Std. 802.11, CDMA, WCDMA, LTE, UMTS, GSM, AMPS, Zigbee and Bluetooth®, etc.

Mobile device 700 of some embodiments may be implemented as a smartphone (or similar electronic device). Depending on the embodiment, mobile device 700 may be made sufficiently small in size to be carried in a hand of an adult human.

Mobile device 700 may also include GPS receiver 755 capable of receiving and acquiring GPS signals 759 via GPS antenna 758. GPS receiver 755 may also process, in whole or in part, acquired GPS signals 759 for estimating a location of a mobile device. In some embodiments, processor(s) 711, memory 740, DSP(s) 712 and/or specialized processors (not shown) may also be utilized to process acquired GPS signals, in whole or in part, and/or calculate an estimated location of mobile device 700, in conjunction with GPS receiver 755. Storage of GPS or other signals may be performed in memory 740 or registers (not shown).

Also shown in FIG. 7, mobile device 700 may include digital signal processor(s) (DSP(s)) 712 connected to the bus 701 by a bus interface 710, processor(s) 711 connected to the bus 701 by a bus interface 710 and memory 740. Bus interface 710 may be integrated with the DSP(s) 712, processor(s) 711 and memory 740. In various embodiments, functions may be performed in response to execution of one or more computer-readable instructions stored in memory 740 such as on a computer-readable storage medium, such as RAM, ROM, FLASH, or disc drive, just to name a few examples. The one or more instructions may be executable by processor(s) 711, specialized processors, or DSP(s) 712. Memory 740 may include a non-transitory computer-readable memory and/or a computer-readable memory that stores software code (programming code, instructions, etc.) that are executable by processor(s) 711 and/or DSP(s) 712 to perform functions described herein. In a particular implementation, wireless transceiver 721 may communicate with processor(s) 711 and/or DSP(s) 712 through bus 701 to enable mobile device 700 to be configured as a wireless station. Processor(s) 711 and/or DSP(s) 712 may perform methods and functions, and execute instructions to execute one or more aspects of processes/methods discussed in connection with FIGS. 2A, 3, 4, 5 and 6.

Also shown in FIG. 7, a user interface 735 may include any one of several devices such as, for example, a speaker, microphone, display device, vibration device, keyboard, touch screen, etc. A user interface signal provided to a user may be one or more outputs provided by any of the speaker, microphone, display device, vibration device, keyboard, touch screen, etc. In a particular implementation, user interface 735 may enable a user to interact with one or more applications hosted on mobile device 700. For example, devices of user interface 735 may store digital signals in memory 740 to be further processed by DSP(s) 712 or processor 711 in response to action from a user. Similarly, applications hosted on mobile device 700 may store digital signals in memory 740 to present an output signal to a user. In another implementation, mobile device 700 may optionally include a dedicated audio input/output (I/O) device 770 comprising, for example, a dedicated speaker, microphone, digital to analog circuitry, analog to digital circuitry, amplifiers and/or gain control. In another implementation, mobile device 700 may include touch sensors 762 responsive to touching, pressure, or ultrasonic signals on a keyboard or touch screen device.

Mobile device 700 may also include a dedicated camera device 764 for capturing still or moving imagery. Dedicated camera device 764 may include, for example an imaging sensor (e.g., charge coupled device or CMOS imager), lens, analog to digital circuitry, frame buffers, etc. In one implementation, additional processing, conditioning, encoding or compression of signals representing captured images may be performed at processor 711 or DSP(s) 712. Alternatively, a dedicated video processor 768 may perform conditioning, encoding, compression or manipulation of signals representing captured images. Additionally, dedicated video processor 768 may decode/decompress stored image data for presentation on a display device (not shown) on mobile device 700.

Mobile device 700 may also include sensors 760 coupled to bus 701 which may include, for example, inertial sensors and environmental sensors. Inertial sensors of sensors 760 may include, for example accelerometers (e.g., collectively responding to acceleration of mobile device 700 in three dimensions), one or more gyroscopes or one or more magnetometers (e.g., to support one or more compass applications). Environmental sensors of mobile device 700 may include, for example, temperature sensors, barometric pressure sensors, ambient light sensors, and camera imagers, microphones, just to name few examples. Sensors 760 may include one or more ultrasonic fingerprint sensors. Sensors 760 may generate analog signals that may be converted to digital signals using an analog-to-digital converter (ADC). Alternatively, sensors 760 may generate digital signals. The digital signals are stored in memory 740 and processed by DPS(s) or processor 711 in support of one or more applications such as, for example, applications directed to measuring heart rate and/or respiration rate and/or applications directed to positioning or navigation operations.

In a particular implementation, mobile device 700 may include a dedicated modem processor 766 capable of performing baseband processing of signals received and down-converted at wireless transceiver 721 or GPS receiver 755. Similarly, dedicated modem processor 766 may perform baseband processing of signals to be up-converted for transmission by wireless transceiver 721. In alternative implementations, instead of having a dedicated modem processor, baseband processing may be performed by a processor or DSP (e.g., processor 711 or DSP(s) 712).

Figure 8A:
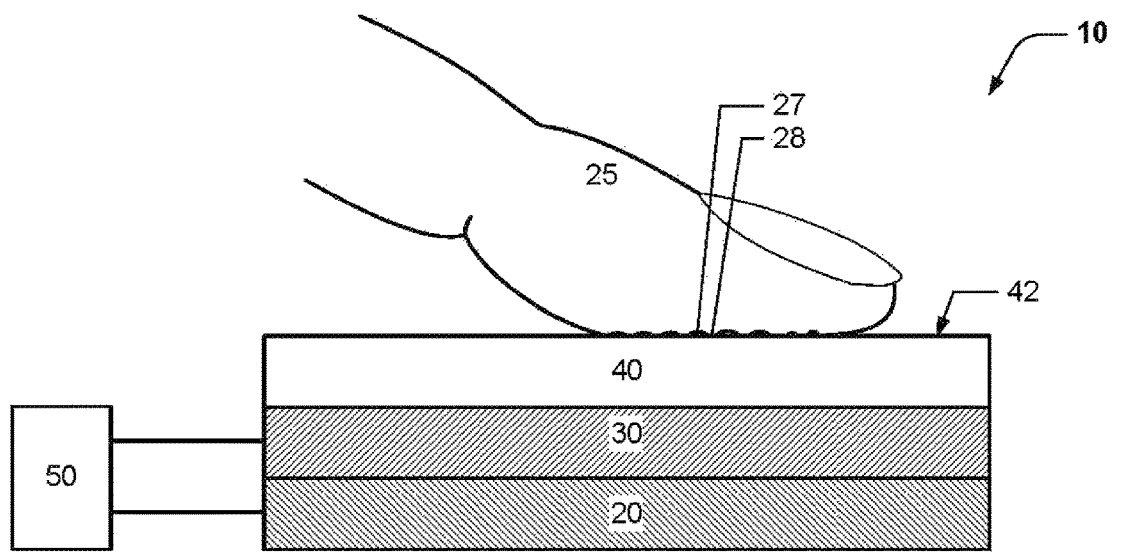
FIGS. 8A-8C illustrate an example of an ultrasonic fingerprint sensor according to aspects of the present disclosure.
Figure 8B:
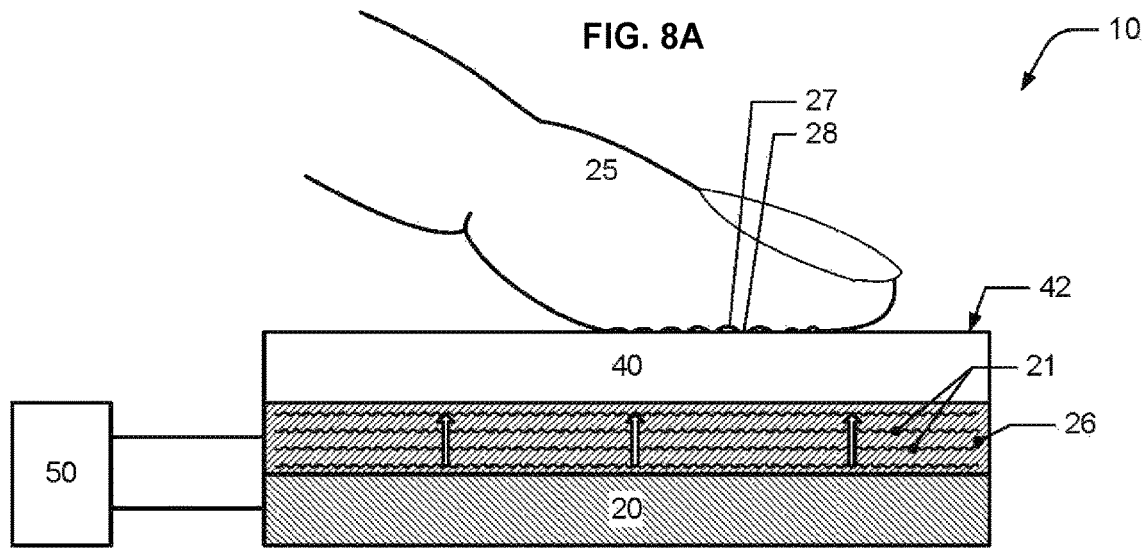
Figure 8C:
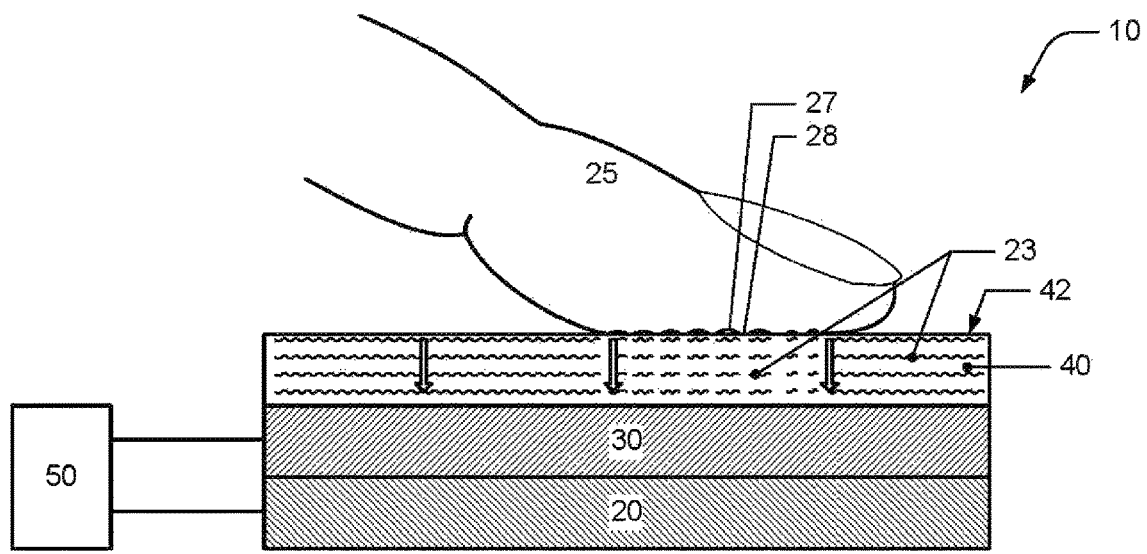

FIGS. 8A-8C illustrate an example of an ultrasonic fingerprint sensor according to aspects of the present disclosure. As shown in FIG. 8A, an ultrasonic fingerprint sensor 10 may include an ultrasonic transmitter 20 and an ultrasonic receiver 30 under a platen 40. The ultrasonic transmitter 20 may be a piezoelectric transmitter that can generate ultrasonic waves 21 (see FIG. 8B). The ultrasonic receiver 30 may include a piezoelectric material and a two dimensional array of pixel circuits (e.g. in an ultrasonic sensor pixel circuit array, shown in FIG. 9B), disposed in or on a substrate. In some implementations, the substrate may be a glass, plastic or semiconductor substrate such as a silicon substrate. In operation, the ultrasonic transmitter 20 may generate one or more ultrasonic waves that travel through the ultrasonic receiver 30 to the exposed surface 42 of the platen 40. At the exposed surface 42 of the platen 40, the ultrasonic energy may be transmitted, absorbed or scattered by an object 25 that is in contact with the platen 40, such as the skin of a fingerprint ridge 28, or reflected back. In those locations where air contacts the exposed surface 42 of the platen 40, e.g., valleys 27 between fingerprint ridges 28, most of the ultrasonic wave will be reflected back toward the ultrasonic receiver 30 for detection (see FIG. 8C). In some embodiments, ultrasonic fingerprint sensor 10 in FIGS. 8A-8C supports (and is used to implement), means for sensing ultrasound.

Control electronics 50 may be coupled to the ultrasonic transmitter 20 and ultrasonic receiver 30 and may supply timing signals that cause the ultrasonic transmitter 20 to generate one or more ultrasonic waves 21. The control electronics 50 may then receive signals from the ultrasonic receiver 30 that are indicative of reflected ultrasonic energy (also called acoustic energy) 23. The control electronics 50 may use output signals received from the ultrasonic receiver 30 to construct a three-dimensional image of the object 25. In some implementations, the control electronics 50 may also, over time, successively sample the output signals to detect movement of structures within object 25. In some embodiments, control electronics 50 in FIGS. 8A-8C supports (and is used to implement), means for controlling the operations of the ultrasonic fingerprint sensor, as well as means for controlling the operations of the methods described herein.

According to aspects of the present disclosure, the ultrasonic transmitter 20 may be a plane wave generator including a substantially planar piezoelectric transmitter layer. Ultrasonic waves may be generated by applying a voltage to the piezoelectric layer to expand or contract the layer, depending upon the signal applied, thereby generating a plane wave. The voltage may be applied to the piezoelectric transmitter layer via a first transmitter electrode and a second transmitter electrode. In this fashion, an ultrasonic wave may be made by changing the thickness of the layer via a piezoelectric effect. This ultrasonic wave travels toward a finger (or other object), passing through the platen 40. A portion of the wave not absorbed or transmitted into a finger may be reflected, so as to pass back through the platen 40 and be received by the ultrasonic receiver 30. The first and second transmitter electrodes may be metallized electrodes, for example, metal layers that coat opposing sides of the piezoelectric transmitter layer.

The ultrasonic receiver 30 may include a two dimensional array of pixel circuits disposed in or on a substrate, which also may be referred to as a wafer or a backplane, and a piezoelectric receiver layer. In some implementations, each pixel circuit may include one or more silicon or thin-film transistor (TFT) elements, electrical interconnect traces and, in some implementations, one or more additional circuit elements such as diodes, capacitors, and the like. Each pixel circuit may be configured to convert an electric charge generated in the piezoelectric receiver layer proximate to the pixel circuit into an electrical signal. Each pixel circuit may include a pixel input electrode that electrically couples the piezoelectric receiver layer to the pixel circuit.

Figure 9A:
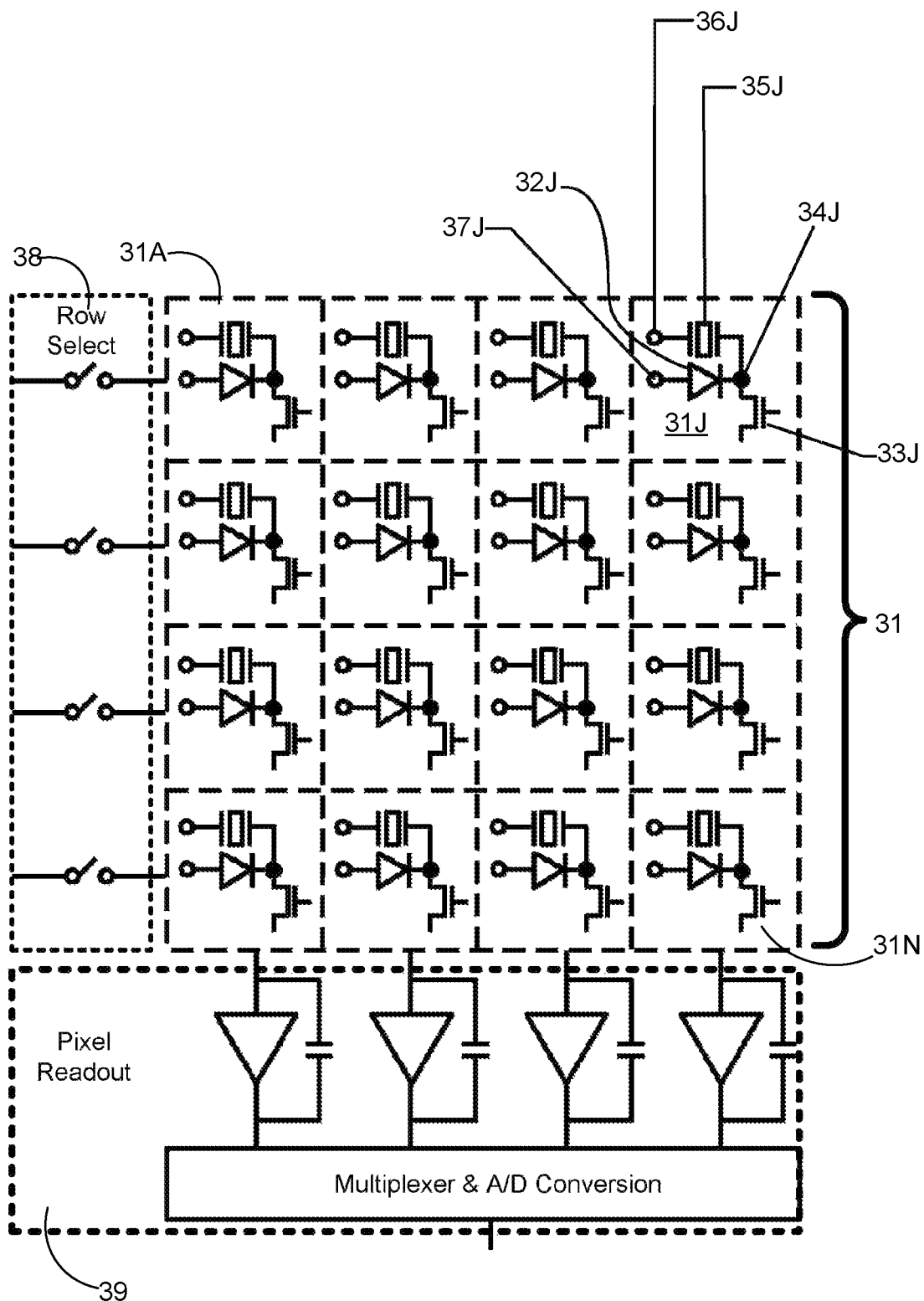
FIG. 9A illustrates an example of a four-by-four array of sensor pixels for an ultrasonic sensor array according to aspects of the present disclosure.

In the illustrated implementation, a receiver bias electrode is disposed on a side of the piezoelectric receiver layer proximal to platen 40. The receiver bias electrode may be a metallized electrode and may be grounded or biased to control which signals are passed to the silicon or TFT sensor array. Ultrasonic energy that is reflected from the exposed (top) surface 42 of the platen 40 is converted into localized electrical charges by the piezoelectric receiver layer. These localized charges are collected by the pixel input electrodes and are passed on to the underlying pixel circuits. The charges may be amplified by the pixel circuits and provided to the control electronics, which processes the output signals. A simplified schematic of an example pixel circuit is shown in FIG. 9A, however one of ordinary skill in the art will appreciate that many variations of and modifications to the example pixel circuit shown in the simplified schematic may be contemplated.

Control electronics 50 may be electrically connected to the first transmitter electrode and the second transmitter electrode, as well as to the receiver bias electrode and the pixel circuits in or on the substrate. The control electronics 50 may operate substantially as discussed previously with respect to FIGS. 8A-8C.

The platen 40 may be any appropriate material that can be acoustically coupled to the receiver, with examples including plastic, ceramic, glass, sapphire, stainless steel, aluminum, a metal, a metal alloy, polycarbonate, a polymeric material, or a metal-filled plastic. In some implementations, the platen 40 may be a cover plate, e.g., a cover glass or a lens glass for a display device or an ultrasonic fingerprint sensor. Detection and imaging may be performed through relatively thick platens if desired, e.g., 3 mm and above.

Examples of piezoelectric materials that may be employed according to various implementations include piezoelectric polymers having appropriate acoustic properties, for example, acoustic impedance between about 2.5 MRayls and 5 MRayls. Specific examples of piezoelectric materials that may be employed include ferroelectric polymers such as polyvinylidene fluoride (PVDF) and polyvinylidene fluoride-trifluoroethylene (PVDF-TrFE) copolymers. Examples of PVDF copolymers include 60:40 (molar percent) PVDF-TrFE, 70:30 PVDF-TrFE, 80:20 PVDF-TrFE, and 90:10 PVDR-TrFE. Other examples of piezoelectric materials that may be employed include polyvinylidene chloride (PVDC) homopolymers and copolymers, polytetrafluoroethylene (PTFE) homopolymers and copolymers, and diisopropylammonium bromide (DIPAB).

The thickness of each of the piezoelectric transmitter layer and the piezoelectric receiver layer may be selected so as to be suitable for generating and receiving ultrasonic waves. In one example, a PVDF piezoelectric transmitter layer may be approximately 28 μm thick and a PVDF-TrFE receiver layer may be approximately 12 μm thick. Example frequencies of the ultrasonic waves are in the range of 5 MHz to 30 MHz, with wavelengths on the order of a quarter of a millimeter or less.

FIGS. 8A-8C show example arrangements of ultrasonic transmitters and ultrasonic receivers included in an ultrasonic fingerprint sensor, with other arrangements possible. For example, in some implementations, the ultrasonic transmitter 20 may be above the ultrasonic receiver 30, i.e., closer to the object of detection. In some implementations, the piezoelectric receiver layer may serve as both an ultrasonic transmitter and an ultrasonic receiver. A piezoelectric layer that may serve as either an ultrasonic transmitter or an ultrasonic receiver may be referred to as a piezoelectric transceiver layer or as a single-layer transmitter/receiver layer. In some implementations, the ultrasonic fingerprint sensor may include an acoustic delay layer. For example, an acoustic delay layer may be incorporated into the ultrasonic fingerprint sensor 10 between the ultrasonic transmitter 20 and the ultrasonic receiver 30. An acoustic delay layer may be employed to adjust the ultrasonic pulse timing, and at the same time electrically insulate the ultrasonic receiver 30 from the ultrasonic transmitter 20. The delay layer may have a substantially uniform thickness, with the material used for the delay layer and/or the thickness of the delay layer selected to provide a desired delay in the time for reflected ultrasonic energy to reach the ultrasonic receiver 30. In doing so, the range of time during which an energy pulse that carries information about the object by virtue of having been reflected by the object may be made to arrive at the ultrasonic receiver 30 during a time range when it is unlikely that energy reflected from other parts of the ultrasonic fingerprint sensor 10 is arriving at the ultrasonic receiver 30. In some implementations, the silicon or TFT substrate and/or the platen 40 may serve as an acoustic delay layer.

FIG. 9A depicts a 4×4 subarray of pixel circuits 31A . . . 31J . . . 31N in an ultrasonic sensor pixel circuit array 31 included in an ultrasonic receiver 30 (FIGS. 8A-8C) which in turn is included within an ultrasonic fingerprint sensor 10 (FIGS. 8A-8C). Each pixel circuit 31J (FIG. 9A) may, for example, be associated with a local region of piezoelectric sensor material 35J, a receive bias electrode 36J, a diode bias voltage electrode 37J, a pixel input electrode 34J, a peak detection diode 32J and a readout transistor 33J; many or all of these elements may be formed on or in the backplane to form pixel circuit 31J. In practice, the local region of piezoelectric sensor material 35J of each pixel circuit 31J may transduce received ultrasonic energy into electrical charges. The peak detection diode 32J may register the maximum amount of charge detected by the local region of piezoelectric sensor material 35J. Each row of the ultrasonic sensor pixel circuit array 31 (FIGS. 8A-8C) may be scanned, e.g., through a row select mechanism 38, a gate driver, or a shift register, and the readout transistor 33J for each column may be triggered to allow the magnitude of the peak charge for each pixel circuit 31J to be read by pixel readout circuitry 39 which may include, e.g., a multiplexer and an A/D converter. The ultrasonic sensor pixel circuit array 31 (FIGS. 8A-8C) may include one or more silicon transistors or TFTs to allow gating, addressing, and resetting of the pixel circuits 31A . . . 31J . . . 31N.

Each pixel circuit 31J may provide information about a small portion of the object (such as finger of a user) detected by the ultrasonic fingerprint sensor 10. While, for convenience of illustration, the example shown in FIG. 9A is of a relatively coarse resolution, ultrasonic fingerprint sensors having a resolution on the order of 500 pixels per inch or higher may be configured with a layered structure. The detection area of the ultrasonic fingerprint sensor 10 may be selected depending on the intended object of detection. For example, the detection area (e.g., active area) may range from about 5 mm×5 mm for a single finger to about 3 inches×3 inches for four fingers. Smaller and larger areas, including square, rectangular and non-rectangular geometries, may be used as appropriate for the object.

Figure 9B:
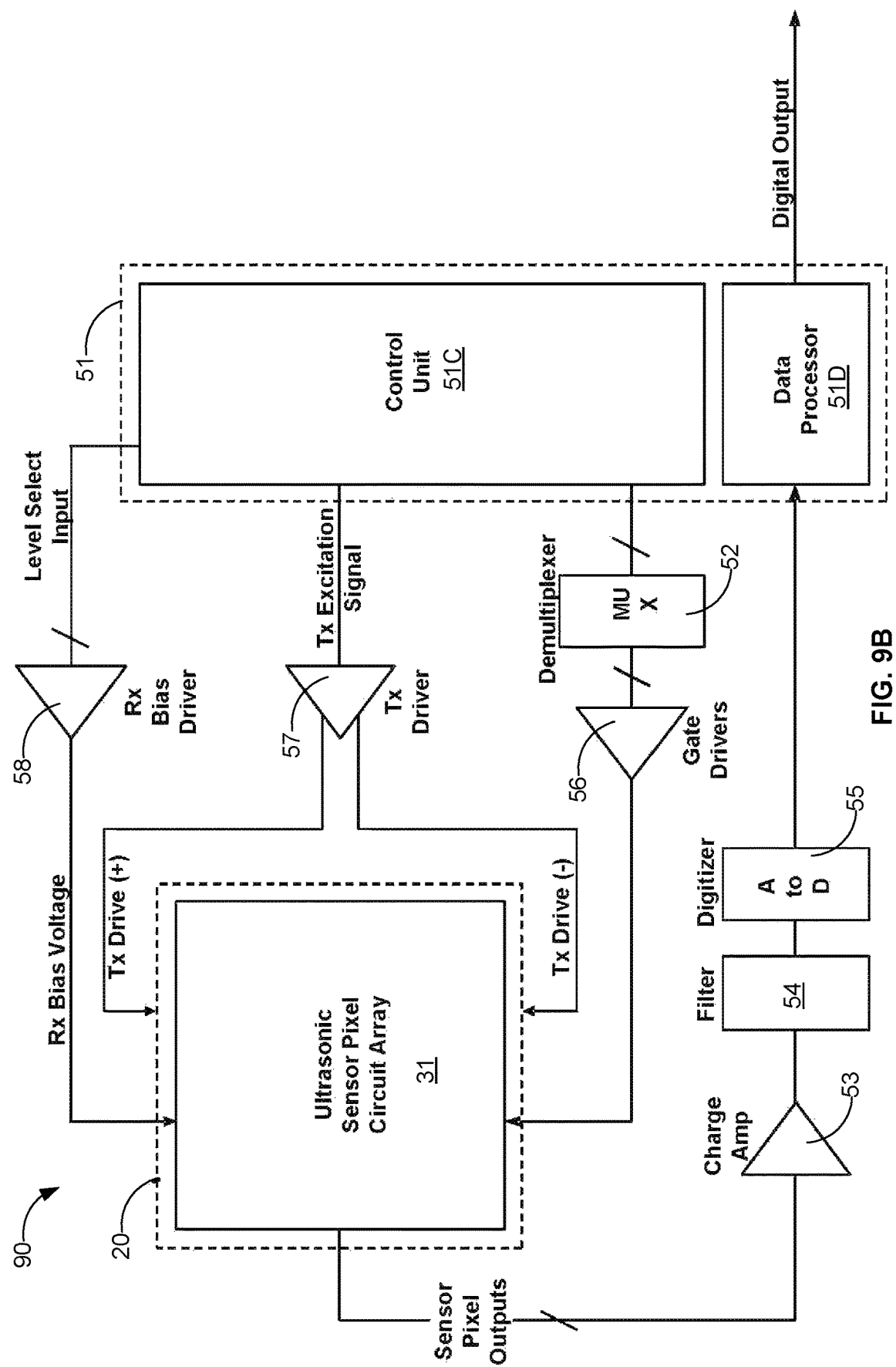
FIG. 9B illustrates an example of a high-level block diagram of an ultrasonic sensor system according to aspects of the present disclosure.

FIG. 9B shows an example of a high-level block diagram of an ultrasonic sensor system 90. All elements shown in FIG. 9B, except for ultrasonic sensor pixel circuit array 31 and ultrasonic transmitter 20, may form part of control electronics 50. Thus, control electronics 50 may include a sensor controller 51 (e.g. in a microcontroller of an ASIC described above) that in turn may include a control unit 51C configured to control various aspects of sensor system 90, e.g., ultrasonic transmitter 20's timing and excitation waveforms, bias voltages for the ultrasonic receiver 30 and pixel circuits 31A . . . 31J . . . 31N, pixel addressing, signal filtering and conversion, readout frame rates, and so forth. The sensor controller 51 may also include a data processor 51D that receives data from the ultrasonic sensor pixel circuit array 31. The data processor 51D may translate the digitized data into image data of a fingerprint or format the data for further processing.

For example, the control unit 51C may send a transmitter (Tx) excitation signal to a Tx driver at regular intervals to cause the Tx driver 57 to excite the ultrasonic transmitter 20 and produce planar ultrasonic waves. The control unit 51C may send level select input signals through a receiver (Rx) bias driver 58 to bias the receive bias electrode 36J and allow gating of acoustic signal detection by the pixel circuits 31A . . . 31J . . . 31N. A demultiplexer 52 may be used to turn on and off gate drivers 56 that cause a particular row or column of pixel circuits 31A . . . 31J . . . 31N to provide sensor output signals. Output signals from the pixel circuits 31A . . . 31J . . . 31N may be sent through a charge amplifier 53, a filter 54 such as an RC filter or an anti-aliasing filter, and a digitizer 55 to the data processor 51D. Note that portions of the system 90 may be included on the silicon or TFT substrate and other portions may be included in an associated integrated circuit (e.g., an ASIC).

According to aspects of the present disclosure, an ultrasonic fingerprint sensor may be configured to produce high-resolution fingerprint images for user verification and authentication. In some implementations, the ultrasonic fingerprint sensor may be configured to detect reflected signals proportional to the differential acoustic impedance between an outer surface of a platen and a finger ridge (tissue) and valley (air). For example, a portion of the ultrasonic wave energy of an ultrasonic wave may be transmitted from the sensor into finger tissue in the ridge areas (and used, for example, in measuring heart rate and/or respiration rate as described herein), while the remaining portion of the ultrasonic wave energy is reflected back towards the sensor, whereas a smaller portion of the wave may be transmitted into the air in the valley regions of the finger while the remaining portion of the ultrasonic wave energy is reflected back to the sensor.

As described herein, memory 110 and/or memory 740 may provide means for storing data associated with the operation of the mobile devices and/or ultrasonic fingerprint sensors described herein. Sensor subsystem 106, sensors 760 and/or ultrasonic fingerprint sensor 10 may provide means for sensing ultrasound as well as means for transmitting acoustic energy toward a finger of a user and for receiving one or more reflections of ultrasonic energy from the finger. Controller 104, applications module 108, control electronics 50, sensor controller 51, processor 711, and/or DSP 712 may provide means for controlling the operation of the mobile device, the ultrasonic fingerprint sensor, and/or the blocks of the methods described herein. For example, controller 104, applications module 108, control electronics 50, sensor controller 51, processor 711, and/or DSP 712 may provide means for controlling or operating the means for sensing ultrasound to transmit acoustic energy at a first frequency toward a surface of a finger (e.g. see block 202A in FIG. 2C), and for controlling or operating the means for sensing ultrasound to capture a first snapshot of one or more reflections of the acoustic energy at the first frequency from the surface of the finger (e.g. see block 202B in FIG. 2C). Controller 104, applications module 108, control electronics 50, sensor controller 51, processor 711, and/or DSP 712 may also store in the means for storing, a plurality of first measurements in the first snapshot (e.g. see block 203 in FIG. 2C). Controller 104, applications module 108, control electronics 50, sensor controller 51, processor 711, and/or DSP 712 may repeatedly operate the means for sensing ultrasound over a window of time to transmit acoustic energy toward the surface of the finger, the acoustic energy being transmitted at a second frequency that is lower than the first frequency (e.g. see block 204A in FIG. 2C), and capture a sequence of sets, each set comprising one or more second snapshots of reflection of the acoustic energy at the second frequency from one or more depths within the finger (e.g. see block 204B in FIG. 2C). Controller 104, applications module 108, control electronics 50, sensor controller 51, processor 711, and/or DSP 712 may furthermore store in the means for storing, each plurality of second measurements in each second snapshot in said each set in the sequence (e.g. see block 205 in FIG. 2C). It should be recognized that controller 104, applications module 108, control electronics 50, sensor controller 51, processor 711, and/or DSP 712 may be programmed using computer-readable instructions stored in memory 110 and/or memory 740 to perform the functions described herein, including but not limited to, the algorithms embodied in the blocks of the methods described in FIGS. 2A and 3-6.

The methodologies described herein may be implemented by various means depending upon applications according to particular examples. For example, such methodologies may be implemented in hardware, firmware, software, or combinations thereof. In a hardware implementation, for example, a processing unit may be implemented within one or more application specific integrated circuits ("ASICs"), digital signal processors ("DSPs"), digital signal processing devices ("DSPDs"), programmable logic devices ("PLDs"), field programmable gate arrays ("FPGAs"), processors, controllers, micro-controllers, microprocessors, electronic devices, other devices units designed to perform the functions described herein, or combinations thereof.

Some portions of the detailed description included herein are presented in terms of algorithms or symbolic representations of operations on binary digital signals stored within a memory of a specific apparatus or special purpose computing device or platform. In the context of this particular specification, the term specific apparatus or the like includes a general purpose computer once it is programmed to perform particular operations pursuant to instructions from program software. Algorithmic descriptions or symbolic representations are examples of techniques used by those of ordinary skill in the signal processing or related arts to convey the substance of their work to others skilled in the art. An algorithm is here, and generally, is considered to be a self-consistent sequence of operations or similar signal processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals, or the like. It should be understood, however, that all of these or similar terms are to be associated with appropriate physical quantities and are merely convenient labels. Unless specifically stated otherwise, as apparent from the discussion herein, it is appreciated that throughout this specification discussions utilizing terms such as "processing," "computing," "calculating," "determining" or the like refer to actions or processes of a specific apparatus, such as a special purpose computer, special purpose computing apparatus or a similar special purpose electronic computing device. In the context of this specification, therefore, a special purpose computer or a similar special purpose electronic computing device is capable of manipulating or transforming signals, typically represented as physical electronic or magnetic quantities within memories, registers, or other information storage devices, transmission devices, or display devices of the special purpose computer or similar special purpose electronic computing device.

The terms, "and," and "or" as used herein may include a variety of meanings that will depend at least in part upon the context in which it is used. Typically, "or" if used to associate a list, such as A, B or C, is intended to mean A, B, and C, here used in the inclusive sense, as well as A, B or C, here used in the exclusive sense. Reference throughout this specification to "one example" or "an example" means that a particular feature, structure, or characteristic described in connection with the example is included in at least one example of claimed subject matter. Thus, the appearances of the phrase "in one example" or "an example" in various places throughout this specification are not necessarily all referring to the same example. Furthermore, the particular features, structures, or characteristics may be combined in one or more examples. Examples described herein may include machines, devices, engines, or apparatuses that operate using digital signals. Such signals may include electronic signals, optical signals, electromagnetic signals, or any form of energy that provides information between locations.

While there has been illustrated and described what are presently considered to be example features, it will be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter may also include all aspects falling within the scope of the appended claims, and equivalents thereof.

We claim:

1. A method comprising:
    operating an ultrasonic fingerprint sensor with a controller to:
        transmit acoustic energy toward a surface of a finger over a window of time; and
        capture a sequence of sets over the window of time, each set comprising one or more subdermal snapshots of one or more reflections of the acoustic energy from one or more depths within the finger;
    storing in memory, for each location sampled in the finger, a sequence of measurements indexed by time for a plurality of measurements from each subdermal snapshot in each set in the sequence;
    determining that a signal oscillating at a rate within a predetermined range of oscillation of an internal organ of a human is not present in the sequence of measurements indexed by time; and
    iteratively increasing the window of time and repeating the operating the ultrasonic fingerprint sensor, the storing in the memory, and determining whether the signal oscillating at the rate within the predetermined range of oscillation of the internal organ of the human is present, within a predetermined number of iterations, until the signal oscillating at the rate within the predetermined range of oscillation of the internal organ of the human is determined to be present.

2. The method of claim 1 wherein:
    the window of time has a duration of at least 3 seconds during a first transmission of the acoustic energy toward the surface of the finger.

3. The method of claim 1, wherein:
    the window of time is increased by 1 second in each iteration after no signal oscillating at the rate within the predetermined range of oscillation of the internal organ of the human is determined to be present.

4. The method of claim 1 wherein:
    the internal organ is a heart and the signal oscillating is a heart rate;
    a lower limit of the predetermined range of oscillation is 40 cycles per minute; and an upper limit of the predetermined range of oscillation is 200 cycles per minute.

5. The method of claim 1 wherein:
the internal organ is lungs and the signal oscillating is a respiration rate;
a lower limit of the predetermined range of oscillation is 8 cycles per minute; and
an upper limit of the predetermined range of oscillation is 40 cycles per minute.

6. The method of claim 1 wherein the determining comprises:
applying a low pass filter to each subdermal snapshot to obtain each sequence of measurements indexed by time;
applying a bandpass filter to each sequence of measurements indexed by time to remove any signal that oscillates in time below a lower limit, above an upper limit, or a combination thereof to obtain a bandpass filtered sequence for each location sampled in the finger;
determining a statistical variance for each bandpass filtered sequence for each location sampled in the finger; and
identifying one or more active locations in the finger based on the statistical variance for each bandpass filtered sequence for each location sampled in the finger.

7. The method of claim 6 wherein the identifying the one or more active locations in the finger further comprises:
ranking each location sample in the finger, based on the statistical variance of each bandpass filtered sequence generated by the bandpass filter; and
selecting the one or more active locations which have highest statistical variances.

8. The method of claim 7, further comprising:
measuring at least one of a heart rate or a respiration rate, or the combination thereof at the one or more active locations in the finger comprising:
applying a Fourier transform to each temporal sequence corresponding to each of the one or more active locations to obtain a group of frequency domain vectors;
combining the group of frequency domain vectors into a single frequency domain vector;
identifying one or more peaks in the single frequency domain vector; and
using the one or more peaks to determine the at least one of the heart rate or the respiration rate, or the combination thereof.

9. An apparatus comprising:
a memory;
an ultrasonic fingerprint sensor; and
a controller coupled to the memory and the ultrasonic fingerprint sensor;
wherein the controller is configured to:
operate the ultrasonic fingerprint sensor to:
transmit acoustic energy toward a surface of a finger over a window of time; and
capture a sequence of sets over the window of time, each set comprising one or more subdermal snapshots of one or more reflections of the acoustic energy from one or more depths within the finger;
store in the memory, for each location sampled in the finger, a sequence of measurements indexed by time for a plurality of measurements from each subdermal snapshot in each set in the sequence; and
determine that a signal oscillating at a rate within a predetermined range of oscillation of an internal organ of a human is not present in the sequence of measurements indexed by time; and
iteratively increase the window of time and repeat operations of operate the ultrasonic fingerprint sensor and store in the memory, with an operation to determine whether the signal oscillating at the rate within the predetermined range of oscillation of the internal organ of the human is present, within a predetermined number of iterations, until the signal oscillating at the rate within the predetermined range of oscillation of the internal organ of the human is determined to be present.

10. The apparatus of claim 9 wherein:
the window of time has a duration of at least 3 seconds during a first transmission of the acoustic energy toward the surface of the finger.

11. The apparatus of claim 9 wherein the controller is further configured to increase the window of time by 1 second in each iteration after no signal oscillating at the rate within the predetermined range of oscillation of the internal organ of the human is determined to be present.

12. The apparatus of claim 9 wherein:
the internal organ is a heart and the signal oscillating is a heart rate;
a lower limit of the predetermined range of oscillation is approximately 40 cycles per minute; and
an upper limit of the predetermined range of oscillation is approximately 200 cycles per minute.

13. The apparatus of claim 9 wherein:
the internal organ is lungs and the signal oscillating is a respiration rate;
a lower limit of the predetermined range of oscillation is approximately 8 cycles per minute; and
an upper limit of the predetermined range of oscillation is approximately 40 cycles per minute.

14. The apparatus of claim 9 wherein the controller is configured to determine whether the signal is present by being to:
apply a low pass filter to each subdermal snapshot to obtain each sequence of measurements indexed by time;
apply a bandpass filter to each sequence of measurements indexed by time to remove any signal that oscillates in time below a lower limit, above an upper limit, or a combination thereof to obtain a bandpass filtered sequence for each location sampled in the finger;
determine a statistical variance for each bandpass filtered sequence for each location sampled in the finger; and
identify one or more active locations in the finger based on the statistical variance for each bandpass filtered sequence for each location sampled in the finger.

15. The apparatus of claim 14 wherein the controller is configured to identify the one or more active locations in the finger by being configured to:
rank each location sample in the finger, based on the statistical variance for each bandpass filtered sequence generated by the bandpass filter; and
select the one or more active locations which have highest statistical.

16. An apparatus comprising:
means for storing;
means for sensing ultrasound; and
means for controlling coupled to the means for sensing ultrasound;
wherein the means for controlling is configured to:
operate the means for sensing ultrasound to:

transmit acoustic energy toward a surface of a finger over a window of time; and capture a sequence of sets over the window of time, each set comprising one or more subdermal snapshots of one or more reflections of the acoustic energy from one or more depths within the finger;

store in the means for storing, for each location sampled in the finger, a sequence of measurements indexed by time for a plurality of measurements from each subdermal snapshot in each set in the sequence;

determine that a signal oscillating at a rate within a predetermined range of oscillation of an internal organ of a human is not present in the sequence of measurements indexed by time; and iteratively increase the window of time and repeat operations of operate the means for sensing ultrasound and store in the means for storing, with an operation to determine whether the signal oscillating at the rate within the predetermined range of oscillation of the internal organ of the human is present, within a predetermined number of iterations, until the signal oscillating at the rate within the predetermined range of oscillation of the internal organ of the human is determined to be present.

17. The apparatus of claim 16 wherein:
the window of time has a duration of at least 3 seconds during a first transmission of the acoustic energy toward the surface of the finger.

18. The apparatus of claim 16 wherein the means for controlling is further configured to increase the window of time by 1 second in each iteration after no signal oscillating at the rate within the predetermined range of oscillation of the internal organ of the human is determined to be present.

19. The apparatus of claim 16 wherein the means for controlling is configured to determine whether the signal is present by being configured to:

apply a low pass filter to each subdermal snapshot to obtain each sequence of measurements indexed by time;

apply a bandpass filter to each sequence of measurements indexed by time to remove any signal that oscillates in time below a lower limit, above an upper limit, or a combination thereof to obtain a bandpass filtered sequence for each location sampled in the finger;

determine a statistical variance for each bandpass filtered sequence for each location sampled in the finger; and identify one or more active locations in the finger based on the statistical variance for each bandpass filtered sequence for each location sampled in the finger.

20. The apparatus of claim 16 wherein:
the internal organ is a heart and the signal oscillating is a heart rate;
a lower limit of the predetermined range of oscillation is approximately 40 cycles per minute; and
an upper limit of the predetermined range of oscillation is approximately 200 cycles per minute.

21. The apparatus of claim 16 wherein:
the internal organ is lungs and the signal oscillating is a respiration rate;
a lower limit of the predetermined range of oscillation is approximately 8 cycles per minute; and
an upper limit of the predetermined range of oscillation is approximately 40 cycles per minute.

\* \* \* \* \*